(12) United States Patent
McGuinness et al.

(10) Patent No.: US 11,883,420 B2
(45) Date of Patent: *Jan. 30, 2024

(54) STING AGONISTS FOR TREATING BLADDER CANCER AND SOLID TUMORS

(71) Applicants: Venenum Biodesign, LLC, Hamilton, NJ (US); Catherine C. McGuinness, Plainsboro, NJ (US)

(72) Inventors: Brian F. McGuinness, Plainsboro, NJ (US); Grant Gallagher, Milltown, NJ (US); Michael S. McQueney, Philadelphia, PA (US); Rukiye Nazan Eraslan, Robbinsville, NJ (US); Gary Schieven, Lawrenceville, NJ (US); Jason Trama, Cream Ridge, NJ (US); Axel Metzger, Jackson, NJ (US); David J. Diller, East Windsor, NJ (US); David E. Kaelin, Helmatta, NJ (US)

(73) Assignee: VENENUM BIODESIGN, LLC, Hamilton, NJ (US)

( * ) Notice: Subject to any disclaimer, the term of this patent is extended or adjusted under 35 U.S.C. 154(b) by 151 days.

This patent is subject to a terminal disclaimer.

(21) Appl. No.: 17/342,170

(22) Filed: Jun. 8, 2021

(65) Prior Publication Data

US 2021/0290645 A1    Sep. 23, 2021

Related U.S. Application Data

(60) Division of application No. 17/096,416, filed on Nov. 12, 2020, now Pat. No. 11,110,106, which is a continuation-in-part of application No. 16/662,980, filed on Oct. 24, 2019, now Pat. No. 11,161,864.

(60) Provisional application No. 62/785,711, filed on Dec. 28, 2018, provisional application No. 62/751,769, filed on Oct. 29, 2018.

(51) Int. Cl.
  *A61K 31/519*   (2006.01)
  *A61K 31/688*   (2006.01)
  *A61K 9/08*     (2006.01)
  *A61K 9/00*     (2006.01)
  *A61K 39/395*   (2006.01)
  *A61P 35/00*    (2006.01)

(52) U.S. Cl.
  CPC .......... *A61K 31/688* (2013.01); *A61K 9/0019* (2013.01); *A61K 9/0034* (2013.01); *A61K 9/08* (2013.01); *A61K 31/519* (2013.01); *A61K 39/3955* (2013.01); *A61P 35/00* (2018.01)

(58) Field of Classification Search
  CPC .................................................. A61K 31/519
  See application file for complete search history.

(56) References Cited

U.S. PATENT DOCUMENTS

| | | |
|---|---|---|
| 9,724,408 B2 | 8/2017 | Dubensky, Jr. et al. |
| 2016/0068560 A1 | 3/2016 | Patel et al. |
| 2017/0158724 A1 | 6/2017 | Adams et al. |
| 2018/0162899 A1 | 6/2018 | Bignan et al. |
| 2018/0258132 A1 | 9/2018 | Adams et al. |

FOREIGN PATENT DOCUMENTS

| | | |
|---|---|---|
| WO | 2014093936 A1 | 6/2014 |
| WO | 2014189805 A1 | 11/2014 |
| WO | 2015077354 A1 | 5/2015 |
| WO | 2015185565 A1 | 12/2015 |
| WO | 2016096174 A1 | 6/2016 |
| WO | 2016096577 A1 | 6/2016 |
| WO | 2016145102 A1 | 9/2016 |
| WO | 2017027645 A1 | 2/2017 |
| WO | 2017027646 A1 | 2/2017 |
| WO | 2017075477 A1 | 5/2017 |
| WO | 2017093933 A1 | 6/2017 |
| WO | 2017123657 A1 | 7/2017 |
| WO | 2017123669 A1 | 7/2017 |
| WO | 2017161349 A1 | 9/2017 |
| WO | 2018009648 A1 | 1/2018 |
| WO | 2018009652 A1 | 1/2018 |
| WO | 2018045204 A1 | 3/2018 |

(Continued)

OTHER PUBLICATIONS

Bhat N and Fitzgerald KA. "Recognition of Cytosolic DNA by cGAS and other STING-dependent sensors". Eur. Immunol. Mar. 2014; 44(3):634-40 Mar. 2014.
Bundgaard, H., (C) Means to enhance penetration: (1) Prodrugs as a means to improve the delivery of peptide drugs. Adv. Drug Deliv. Rev., 8:1-38 (1992) 1992.
Bundgaard, H., Chapter 5, "Design and Application of Prodrugs," A Textbook of Drug Design and Development, pp. 113-191, Krosgaard-Larsen, P. et al., eds., Harwood Academic Publishers (1991) 1991.

(Continued)

*Primary Examiner* — Brian E McDowell
(74) *Attorney, Agent, or Firm* — Heslin Rothenberg Farley & Mesiti, P.C.

(57) ABSTRACT

Methods for treating bladder cancer and solid tumors are disclosed. The methods include administering to a patient a compound of formula 1

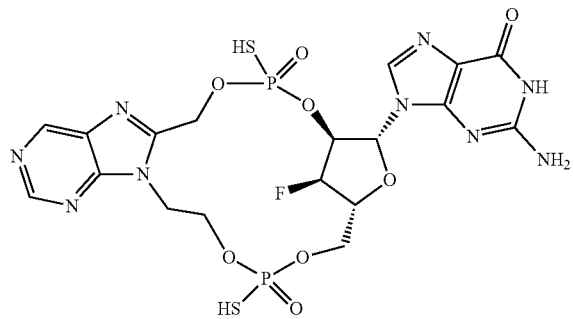

Pharmaceutical compositions of compound 1 are also disclosed.

4 Claims, 14 Drawing Sheets

(56) References Cited

FOREIGN PATENT DOCUMENTS

| | | |
|---|---|---|
| WO | 2018060323 A1 | 4/2018 |
| WO | 2018065360 A1 | 4/2018 |
| WO | 2018098203 A1 | 5/2018 |
| WO | 2018100558 A1 | 6/2018 |
| WO | 2018118664 A1 | 6/2018 |
| WO | 2018118665 A1 | 6/2018 |
| WO | 2018138684 A1 | 8/2018 |
| WO | 2018138685 A1 | 8/2018 |
| WO | 2018156625 A1 | 8/2018 |
| WO | 2018198076 A1 | 11/2018 |
| WO | 2018198084 A1 | 11/2018 |
| WO | 2018208667 A1 | 11/2018 |
| WO | 2019023459 A1 | 1/2019 |
| WO | 2019046496 A1 | 3/2019 |
| WO | 2019046498 A1 | 3/2019 |
| WO | 2019046500 A1 | 3/2019 |
| WO | 2019046511 A1 | 3/2019 |
| WO | 2019074887 A1 | 4/2019 |
| WO | 2019079261 A1 | 4/2019 |
| WO | 2019092660 A1 | 5/2019 |
| WO | 2019118839 A1 | 6/2019 |
| WO | 2019123338 A1 | 6/2019 |
| WO | 2019123339 A1 | 6/2019 |
| WO | 2019123340 A1 | 6/2019 |
| WO | 2019160884 A1 | 8/2019 |

OTHER PUBLICATIONS

Ceron S. et al., The STING agonist 5,6-dimethylxanthenone-4-acetic acid (DMXAA) stimulates an antiviral state and protects mice against herpes simplex virus induced neurological disease. Virology, 2019:529:23-28 2019.

Chen H., et al. "Activation of STAT6 by STING Is Critical for Antiviral Innate Immunity" Cell. 2011, vol. 14: 436-446 2011.

Corrales, L. et al. "Direct activation of STING in the tumor microenvironment leads to potent and systemic tumor regression and immunity" Cell Reports, 2015, vol. 11: 1-13 2015.

Danilchanka, 0. and Mekalanos, JJ. "Cyclic Dinucleotides and the Innate Immune Response" Cell. 2013. vol. 154: 962-970 2013.

Huynh K, Partch CL. Current Protocols in Protein Science: Analysis of protein stability and ligand interactions by thermal shift assay. 2015;79:28.9.1-28.9.14. 2015.

Kakeya, N. et al., Studies on Prodrugs of Cephalosporins. I. Synthesis and Biological Properties of Glycyloxybenzoyloxymethol and Glycylaminobenzoyloxymethyl Esters of 7beta-[2-)2-Aminothiazol-4-yl)-(Z)-2- methoxyiminoacetamido]-3-methyl-3-cephem-4-carboxylic Acid. Chem. Pharm. Bull., 32:692-698 (1984) 1984.

Konno, H. et al. "Cyclic dinucleotides trigger ULK1 (ATG1) phosphorylation of STING to prevent sustained innate mmune signaling" Cell, 2013, vol. 155: 688-698 2013.

Liu S, et al. "Phosphorylation of innate immune adaptor proteins MAVS, Sting, and TRIF induces IRF3 activation" Science. 2015: 347(6227) aaa2630 2015.

Nielsen, N.M. and Bundgaard, H et al., Glycolamide esters as biolabile prodrugs of carboxylic acid agents: Synthesis, stability, bioconversion, and physicochemical properties. J. Pharm. Sci., 77:285 (1988) 1988.

Duyang S., et al. Structural and Functional Analysis of STING Sheds New Light on Cyclic di-GMP Mediated Immune Signaling Mechanism. Immunity. 2012;36(6):10.1016/j.immuni.2012.03.019. doi: 10.1016/j.immuni.2012.03.019 Mar. 19, 2012.

Rader, K., et al. In vivo characterization of site-directed mutations in the promoter of the herpes simplex virus type 1 latency-associated transcripts. J_ Gen. Virol. 1993;74 (Pt 9):1859-1869 1993.

Rautio,J. (editor) Prodrugs and Targeted Delivery (Methods and Principles in Medicinal Chemistry, vol. 47, Wiley-VCH, 2011 2011.

Sun, L. et al. "Cyclic GMP-AMP Synthase Is a Cytosolic DNA Sensor That Activates the Type-I Interferon Pathway" Science, 2013, vol. 339(6121) 2013.

Wang, H., et al., HSV-1 strain McKrae is more neuroinvasive than HSV-1 Kos after corneal or vaginal inoculation in mice. Virus Res. 2013; 173:436-440 2013.

Widder, K., Green, R. eds., Drug and Enzyme Targeting. Methods in Enzymology, 112:309-396, Academic Press 1985) 1985.

Yi, G, et al. "Single Nucleotide Polymorphisms of Human STING Can Affect Innate Immune Response to Cyclic Dinucleotides." PLoS ONE. 2013; 8(10):e77846 2013.

Zhang X, et al. "Cyclic GMP-AMP Containing Mixed Phosphodiester Linkages Is an Endogenous High-Affinity Ligand or STING" Molecular Cell, 2013, vol. 51: 226-235 2013.

Zhong B, et al. "The Adaptor Protein MITA Links Virus-Sensing Receptors to IRF3 Transcription Factor Activation". Immunity. 2008. vol. 29: 538-550 2008.

STING AGONISTS FOR TREATING BLADDER CANCER AND SOLID TUMORS

CROSS REFERENCE TO RELATED APPLICATIONS

This application is a divisional of co-pending U.S. application Ser. No. 17/096,416, filed Nov. 12, 2020, Aug. 15, 2019, U.S. Ser. No. 17/096,416 was a continuation-in-part of U.S. application Ser. No. 16/662,980, filed Oct. 24, 2019, and published as US 2020/0131209 on Apr. 30, 2020. U.S. application Ser. No. 16/662,980 claims the benefit of U.S. Provisional Application Ser. Nos. 62/751,769 and 62/785,711, filed on Oct. 29, 2018 and Dec. 28, 2018, respectively. The entirety of each application is incorporated herein by reference.

FIELD OF THE INVENTION

The invention relates to a method for treating bladder cancer and solid tumors with a 4,9-dimercapto-tetrahydro-19H-3,5,8,10-tetraoxa-4,9-diphospha-1(8,9)-purina-6(4,2)-furanacyclododecaphane 4,9-dioxide. The invention also relates to pharmaceutical compositions containing the compound that are adapted for treating bladder cancer and solid tumors.

BACKGROUND OF THE INVENTION

Non Muscle Invasive Bladder Cancer (NMIBC) is a subset of bladder cancers that represents approximately 70% of the 70,000 new bladder cancer cases diagnosed in the United States each year. Up to 70% of NMIBC cases recur after initial treatment, with 10-20% progressing to muscle invasive bladder cancer. Intravesical instillation of *Mycobacterium bovis Bacillus* Calmette-Guerin (BCG) has been an established therapy for over 40 years. However, approximately 50% of patients fail BCG therapy, increasing the risk of morbidity and death. Patients who fail BCG then require surgical removal of the bladder or chemotherapy and radiation, both of which have considerable morbidity and quality of life issues. BCG-Unresponsive Non Muscle Invasive Bladder Cancer is a recognized subset of Non Muscle Invasive Bladder Cancer. The US FDA has published (2018) a monograph ["BCG-Unresponsive Non Muscle Invasive Bladder Cancer: Developing Drugs and Biologics for Treatment: Guidance for Industry", U.S. Department of Health and Human Services Food and Drug Administration, Center for Drug Evaluation and Research (CDER) Center for Biologics Evaluation and Research (CBER), February 2018] describing the condition and providing guidelines for developing drugs for treating it. There is a substantial need for new therapies for the treatment of NMIBC, including BCG-unresponsive NMIBC.

STING (stimulator of interferon genes), also known as TMEM173, MITA, MPYS, and ERIS, is a transmembrane receptor located inside the cell and a key sensor of cytosolic nucleic acids (Zhong B, et al. "The Adaptor Protein MITA Links Virus-Sensing Receptors to IRF3 Transcription Factor Activation". Immunity. 2008. vol. 29: 538-550). Recent studies have revealed the biology of STING and its role in mobilizing an innate immune response resulting in robust antitumor activity in mouse models.

Activation of the STING pathway results in production of Type I interferons (mainly IFN-α and IFN-β) induced through the IRF3 (interferon regulatory factor 3) pathway. When cGAS binds DNA, its enzyme activity is greatly enhanced, and it produces cyclic GMP-AMP, which serves as a secondary messenger that binds to and activates Stimulator of Interferon Genes (STING), thereby initiating a type 1 interferon immune response.

STING Activation of the STING pathway triggers an immune response that results in generation of specific killer T-cells that can shrink tumors and provide long lasting immunity so the tumors do not recur. The striking antitumor activity obtained with STING agonists in preclinical models has generated a high level of excitement for this target, and small molecule compounds that can modulate the STING pathway have potential to treat both cancer and reduce autoimmune diseases.

The potential therapeutic benefits of enhancing both innate and adaptive immunity make STING an attractive therapeutic target that demonstrates impressive activity by itself and can also be combined with other therapies.

SUMMARY OF THE INVENTION

In one aspect the invention relates to a method for treating bladder cancer comprising administering to a patient in need of treatment for bladder cancer a therapeutically effective amount of a compound of formula 1

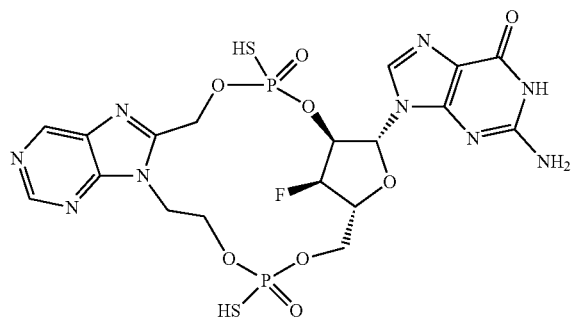 [SMILES: Nc1nc2c(ncn2[C@@H]2O[C@@H]3COP(=O)(S)OCCn4c(nc5cncnc54)COP(=O)(S)O[C@@H]2[C@@H]3F)c(=O)[nH]1]

or pharmaceutically acceptable salt thereof.

In a second aspect, the invention relates to a method for treating solid tumors comprising administering to a patient in need of treatment for a solid tumor a therapeutically effective amount of a compound of formula 1.

In another aspect, the invention relates to a pharmaceutical composition comprising an aqueous carrier and a compound of formula 1.

DETAILED DESCRIPTION

Figure 1:
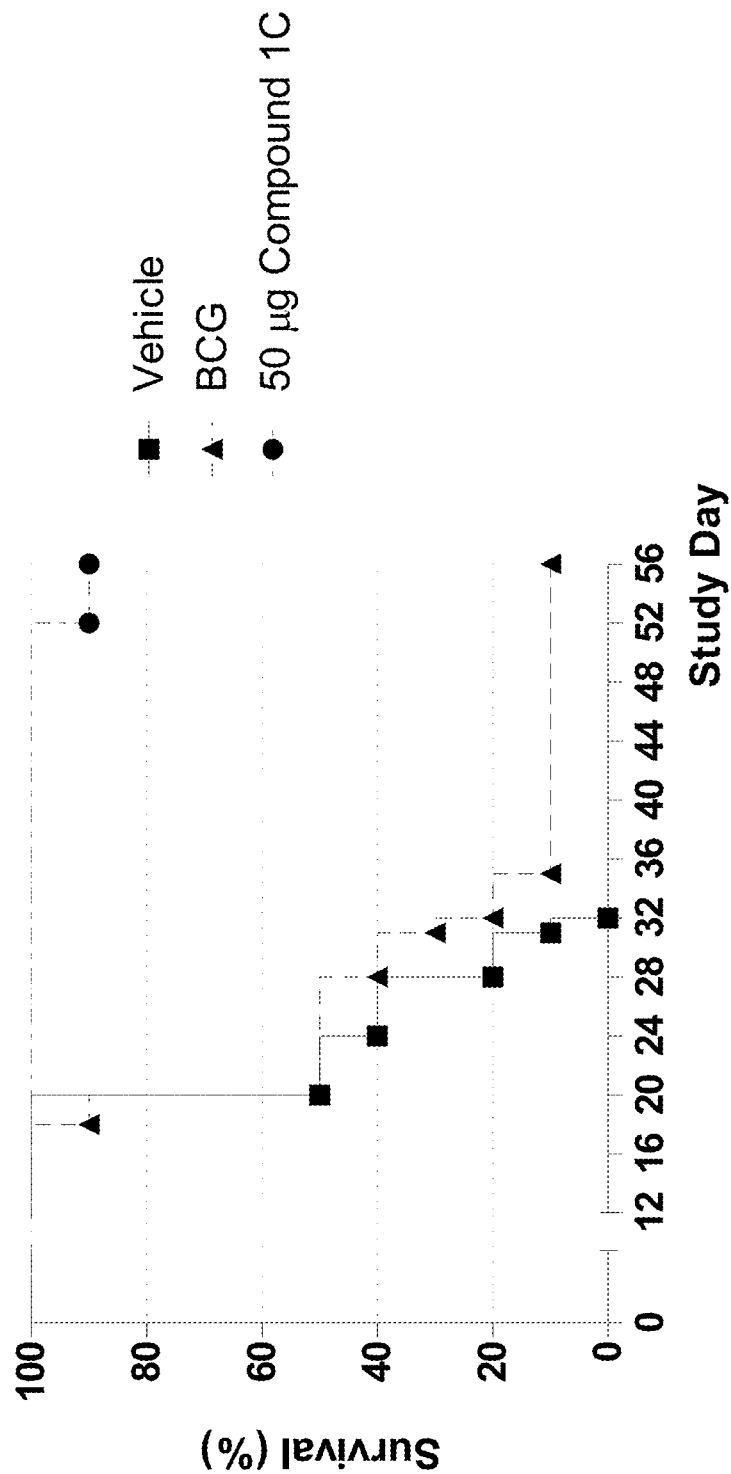
FIG. 1 is a plot of Kaplan Meier survival curves. The difference in survival was significant in the Mantel-Cox log-rank test (P<0.0001).

The compound of formula 1 is a STING agonist that can be administered into the bladder eliciting immunological memory while minimizing systemic exposure. The present method affords better results than existing therapies for NMIBC. The method induces a high level of complete responses in a syngeneic mouse model of NMIBC compared to BCG. For example, treatment with a 1 mg/mL solution of 1C (a substantially pure single isomer of formula 1) in saline in a volume of 40 µL by the intravesical route on a weekly basis for a total of 6 weeks resulted in up to 100% complete responses in the model, compared to only 10% complete responses for BCG therapy on the same schedule. The syngeneic tumor model is a model of BCG-unresponsive NMIBC since the response rate to BCG was low. The rate of complete responses is particularly relevant to human disease since the US FDA (Food and Drug Administration) has designated the complete response rate to be the primary outcome in clinical trials of drugs to treat NMIBC (FDA Guidance to Industry 2018, op. cit.). The duration of response is also very important, as currently approved therapies for NMIBC have been shown to have a have a high rate of recurrent cancer in clinical studies. The new method also induces tumor-specific immunologic memory to the bladder cancer cells. For example, when mice were cured of bladder cancer by treatment with the method of the current invention, all the mice rejected a new inoculation of the same tumor cells with no further treatment. The new method is therefore expected to be of particular benefit in resulting in a greater duration of efficacy.

The present invention provides a method with a route of administration specifically well suited to the treatment of bladder cancer, namely intravesical administration. Intravesical administration is the route currently employed for BCG therapy of bladder cancer. For a drug to be administered by this route, it is essential that the drug be soluble in a pharmaceutically acceptable vehicle for instillation into the bladder. It is additionally advantageous that the drug display minimal systemic exposure relative to the concentration delivered to the bladder tumor to reduce chances of adverse side effects. In the present invention, the method of administration of 1 is shown to be particularly well suited to these requirements. Specifically, 1 is highly soluble in aqueous saline, a preferred vehicle for intravesical administration. Moreover, 1C was found to be rapidly cleared from the circulation, resulting in only low levels of systemic exposure.

It will be recognized that the compound shown as formula 1 contains two unspecified stereocenters in the depiction: the two chiral thiophosphates (phosphorothioates). As a consequence, formula 1 represents four stereoisomers, 1A, 1B, 1C and 1D, which, by virtue of the four chiral centers in the furan ring, are diastereomers of each other and are therefore separable by chromatography. The four isomers are shown:

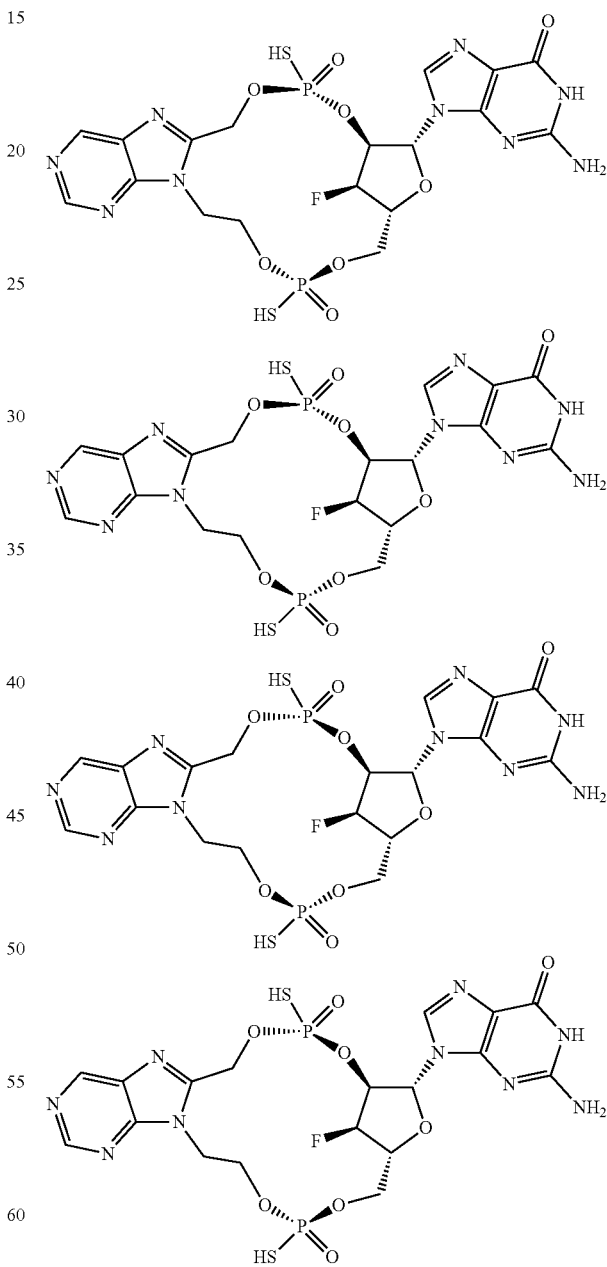

Initial studies, presented in US 2020/0131209, indicated that all four possess STING agonist activity. A particular diastereomer, labeled 1C, was chosen for extensive further study. The absolute configuration of the individual isomers has not yet been confirmed, but each can be characterized and distinguished from the others by its retention time on reverse phase HPLC, as described below and by its phosphorus NMR. Diastereomer 1C exhibits peaks having $^{31}$P NMR (CD$_3$OD) δ 57.05, 56.14.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; a solid line represents connectivity only; it has no stereochemical implication and encompasses all absolute configurations with that connectivity. A wavy line, if present, would indicate disavowal of any stereochemical implication which the bond it represents could generate; in that respect it is equivalent to a solid line. Solid and broken bold lines are geometric descriptors indicating the relative configuration shown but denoting racemic character; and wedge outlines and dotted or broken lines denote enantiomerically pure compounds of indeterminate absolute configuration.

In one embodiment, the present invention relates to a method for treating bladder cancer comprising administering to a patient in need of treatment for bladder cancer a therapeutically effective amount of a compound of formula 1

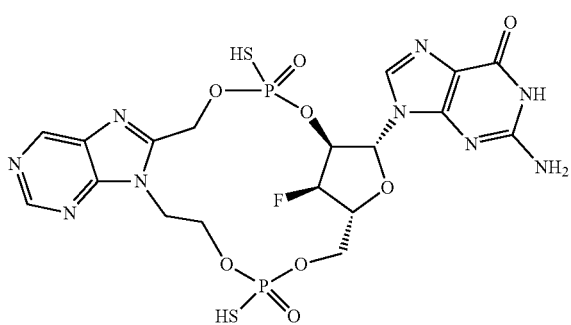 [SMILES: Nc1nc2c(ncn2[C@@H]2O[C@@H]3COP(=O)(S)OCCn4c(nc5cncnc54)COP(=O)(S)O[C@@H]2[C@@H]3F)c(=O)[nH]1]

or pharmaceutically acceptable salt thereof. In some embodiments, the compound is administered as an aqueous solution. In some embodiments, the compound is administered intravesically.

In some embodiments, the bladder cancer is non-muscle-invasive bladder cancer, and in a subset of these, the bladder cancer is BCG-unresponsive Non-Muscle Invasive bladder cancer. In some embodiments of NMIBC, the patient exhibits incomplete or inadequate response to anti-PD1 therapy. An incomplete response is a response to treatment with an anti-PD1 agent that does not result in complete remission or reduction of cell count by at least three orders of magnitude.

In some embodiments, the compound is administered in a solution that provides from 1 mg to 100 mg of compound 1 in a single dose, for example from 50 mg to 100 mg in a single dose. In other embodiments, the compound is administered in a solution that provides from 50 mg to 500 mg of compound 1 in a single dose.

In some embodiments, a solution, as described above, is administered initially as 6 weekly doses. This may then be followed by a maintenance dose, which would be based on clinical judgement of physicians, but is commonly every 1-6 months, in some cases every 3 months.

In another aspect, the invention relates to a method for treating solid tumors comprising administering to a patient in need of treatment for a solid tumor a therapeutically effective amount of a compound of formula 1 or a pharmaceutically acceptable salt thereof. The compound of formula 1 may be the single isomer 1C and the solid tumor may be a colon carcinoma. The compound may be administered as an aqueous solution.

In either of the foregoing methods, treatment with a compound of formula 1 may be accompanied by radiation therapy. "Accompanied by" in this sense means that the same patient is treated for the same tumor or bladder cancer with radiation therapy before, during, or after administration of the compound, as long as the radiation and compound administration are within six months of each other, treatment with a compound of formula 1 may be accompanied by radiation therapy. Similarly, "accompanied by administration of an anti-PD-1 or anti-PD-L1 agent" means that the same patient is treated for the same tumor or bladder cancer with an anti-PD-1 or anti-PD-L1 agent before, during, or after administration of the compound, as long as the anti-PD-1 or anti-PD-L1 agent and compound administration are within twenty-four hours of each other. Examples of anti-PD-1 agents include nivolumab, spartalizumab, dostarlimab, camrelizumab, sintilimab, toripalimab, tislelizumab, and pembrolizumab; examples of anti PD-L1 agents include atezolizumab, avelumab, cosibelimab, envafolimab, and duvalumab. These are representatives of known classes of agents that would be recognized by persons of skill in the art.

In some embodiments, the invention is practiced using a single enantiomer of formula 1 in at least 90%, and preferably at least 95%, stereochemical purity. In these embodiments, isomer 1C is preferred, although 1A, 1B, or 1D, could be used.

In another aspect, the invention relates to pharmaceutical compositions comprising an aqueous carrier and a compound of formula 1

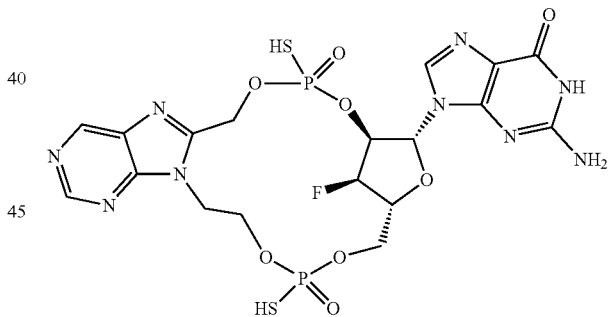

In some embodiments, the compound of formula 1 is present in the pharmaceutical composition as single enantiomer in at least 90%, and preferably at least 95%, stereochemical purity. In these embodiments, isomer 1C is preferred.

In some embodiments, the pharmaceutical composition contains the compound of formula 1 in a concentration from 1 mg/mL to 50 mg/mL. In other embodiments, the pharmaceutical composition contains the compound of formula 1 in a concentration from 1 mg/mL to 10 mg/mL.

As used herein, "treating" or "treatment" refers to obtaining desired pharmacological and/or physiological effect and covers the treatment of a disease-state in a mammal, for example in a human. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The therapeutically effective dose of the STING agonist is a dose that will modulate the STING protein and have an appropriate effect. For example, the dose includes a dose range from 0.0005 mg to about 500 mg inclusive of any particular amount or range therein. In specific embodiments, the dose ranges for humans are from 1 mg to 100 mg or from 50 mg to 250 mg or from 250 mg to 500 mg. It is apparent to one skilled in the art that the therapeutically effective amount will vary with the diseases, syndromes, conditions, and disorders being treated. In order to achieve the therapeutic dose in an aqueous vehicle that is being administered in unit dosages of 10-100 mL, the concentration of compound 1 can be in a concentration from 0.1 mg/mL to 136 mg/mL. It will usually be in the range of 0.1 mg/mL to 10 mg/mL, 1 mg/mL to 50 mg/mL, 1 mg/mL to 10 mg/mL, 5 mg/mL to 10 mg/mL, 1 mg/mL to 5 mg/mL or 10 mg/mL to 20 mg/mL.

Biological Protocols and Results

Eleven week old female C57BL/6 mice were purchased from the Jackson Laboratory West (Sacramento, CA). During the study, the care and use of animals was conducted in accordance with the regulations of the Association for Assessment and Accreditation of Laboratory Animal Care (AAALAC). The protocol and any amendment(s) or procedures involving the care and use of animals in this study was reviewed and approved by the Institutional Animal Care and Use Committee (IACUC) of Invivotek prior the initiation of the study. Mice were group housed (n=4 to 5/cage) and maintained on a 12 hour light and dark schedule. Reverse osmosis chlorinated water and irradiated food Purina rodent diet #5053 (Fisher Feeds, Bound Brook, NJ) were available ad libitum.

For the orthotopic NMIBC MB49-luc mouse model, MB49-luc cells were maintained as monolayer culture in DMEM supplemented with 10% heat inactivated fetal bovine serum at 37° C. and harvested at passage 10. Prior to instillation of MB49-luc cells into the bladder mice were anesthetized through inhalation of 1.5-3.5% isoflurane and a 25 g catheter was inserted through the urethra and the contents of the bladder were then washed out. Each mouse was instilled with a single cell suspension of 95% viable MB49-luc tumor cells at a density of $0.5 \times 10^5$ cells in a volume of 40 µl for 45 minutes.

In the first experiment, using the orthotopic NMIBC MB49-luc mouse model, compound 1C was compared directly to BCG. Mice were assigned into treatment groups on Day 4 post-tumor cell implantation based on bioluminescent imaging (BLI) using IVIS Spectrum (Perkin Elmer). The abdominal regions of the mice were shaved and bioluminescence was measured 14 minutes after intraperitoneal injection of luciferin (3 mg per mouse). The acquired bioluminescent signal (photons/sec) in the region of interest placed over the tumor site was used to measure the size of the tumor. This ensured that each group has approximately the same BLI, to confirm that the tumor size in the bladder was relatively similar prior to treatment. Mice were treated for 2 hours intravesically with compound 1C, BCG or vehicle once weekly for a total of six treatments. Mice were euthanized if they were observed to be in deteriorating condition or had ≥20% loss of body weight. Pseudo survival curves were constructed as mice exited the study due to body weight loss or becoming moribund. The experimental groups are shown in Table 1.

TABLE 1

Treatment outline of the first experiment

| Group # | Treatment | Volume | Animals/group | Treatment Days |
|---|---|---|---|---|
| 1 | Vehicle | 40 µl | 10 | 4, 11, 18, 25, 32 and 39 |
| 2 | 1 mg BCG | 40 µl | 10 | |
| 3 | 50 µg compound 1C | 40 µl | 10 | |

As shown in FIG. 1, BCG was not effective in this model as only 1 of 10 mice survived 56 days following tumor instillation into the bladder. However, treatment with 50 µg compound 1C resulted in the survival of 9 of 10 mice until the study was terminated on Day 56, while all mice in the vehicle group were euthanized by Day 32 due to body weight loss. The difference in survival was significant in the Mantel-Cox log-rank test (P<0.0001).\

Figure 2:
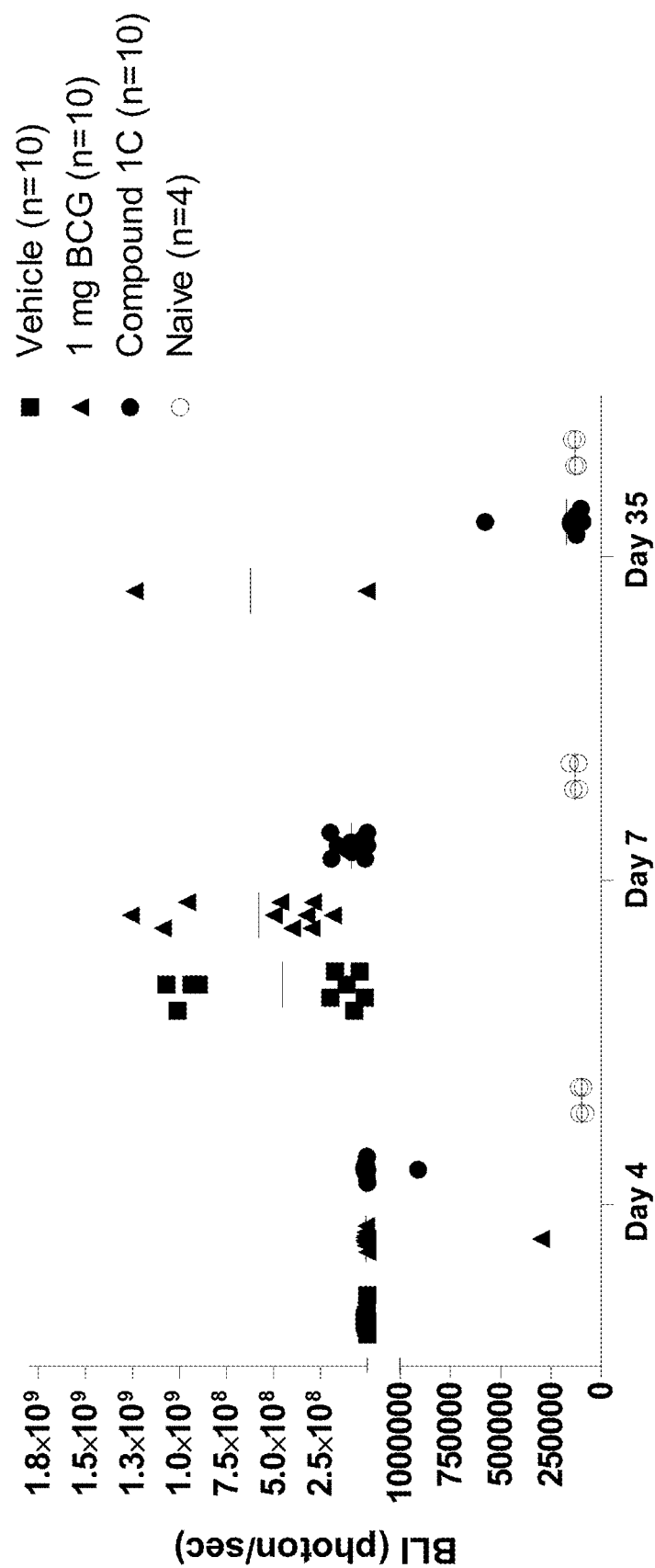
FIG. 2 is a scatterplot of BLI (BioLuminescent Imaging) values on Days 4, 7 and 35 presented as a scatterplot. Black bars indicate the mean value of each group. Only surviving mice are shown for day 35.

Three days after treatment the 50 µg compound 1C group showed suppression of tumor growth relative to the vehicle controls or BCG treated groups. Five weeks after treatment all of the vehicle treated animals were euthanized due to body weight loss and 2 of 10 BCG treated mice showed tumor growth. As shown in FIG. 2, at the five-week time point 9 of 10 mice treated with compound 1C had markedly lower BLI measurements that were similar to the naïve group that was not instilled with MB49-luc cells.

In the second experiment using the orthotopic NMIBC MB49-luc mouse model, three doses of compound 1C and vehicle were delivered via intravesical instillation into the bladder every seven days for a total of six treatments as shown in Table 2. BLI values were used to randomize the mice on Day 4 to group the animals before staring treatment. A non-tumor bearing naïve control group was included.

TABLE 2

Treatment outline of the second experiment

| Group # | Treatment | Volume | Animals/group | Treatment Days |
|---|---|---|---|---|
| 1 | Vehicle | 40 µl | 10 | 4, 11, 18, 25, 32 and 39 |
| 2 | 30 µg compound 1C | 40 µl | 10 | |
| 3 | 40 µg compound 1C | 40 µl | 10 | |
| 4 | 50 µg compound 1C | 40 µl | 11 | |
| 5 | Naïve | 40 µl | 3 | |

Figure 3:
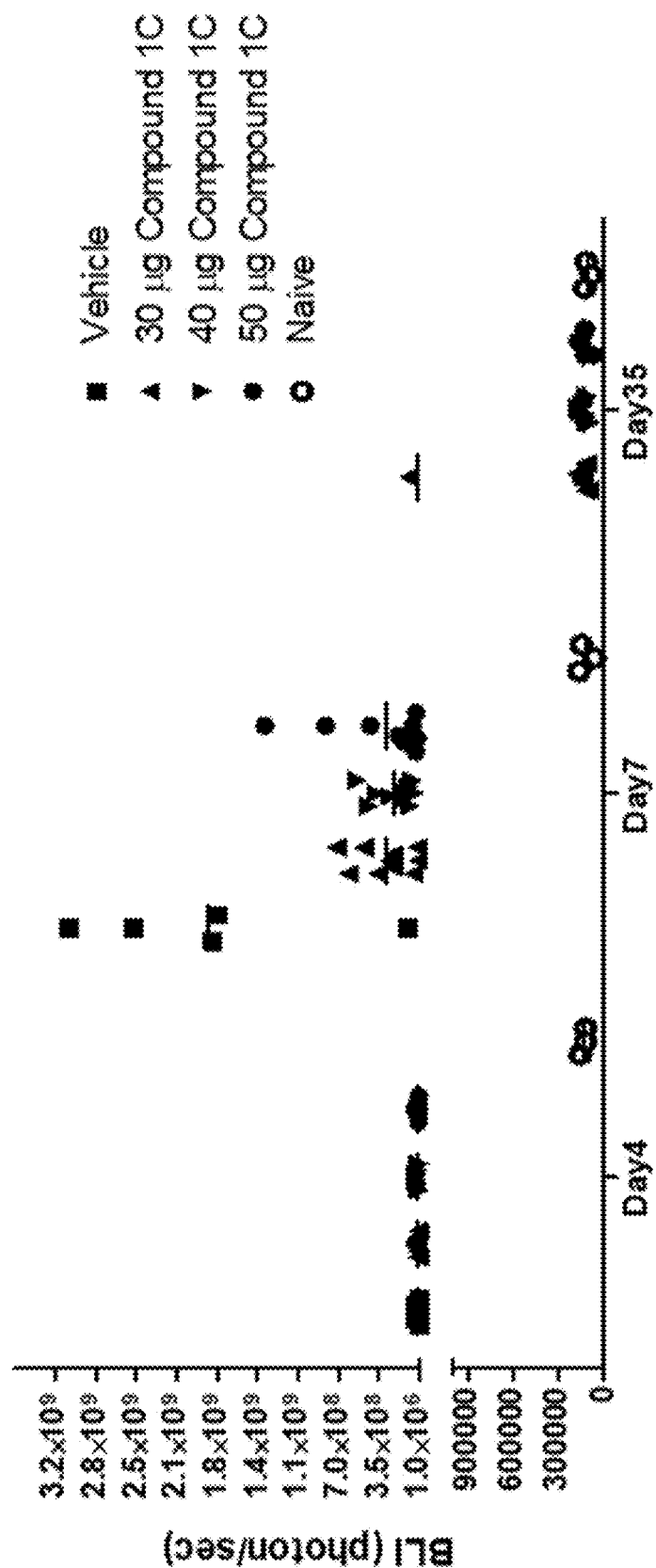
FIG. 3 is a scatterplot of tumor kinetics by BLI before treatment (Day 4) and after the first treatment (Day 7) and fifth treatment (Day 35); the horizontal bars represent the group mean.

BLI values from the initial challenge are shown as a scatterplot in FIG. 3 for Days 4, 7 and 35 to show the anti-tumor effects over time. The 40 µg dose appeared the lowest most efficacious dose, providing a rapid onset of action as tumor growth inhibition was observed by Day 7 and resulted in 100% of animals responding by Day 35.

Figure 4:
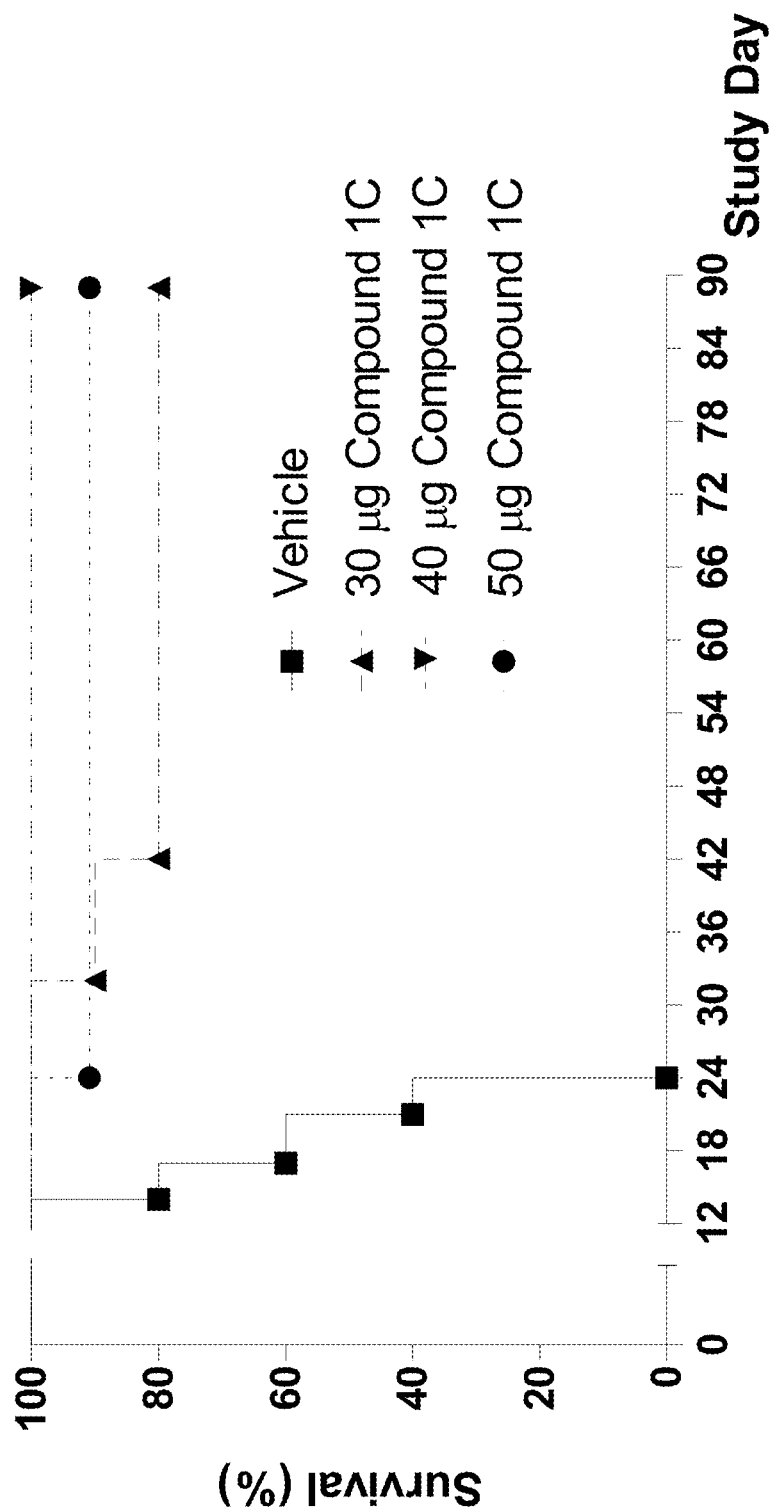
FIG. 4 is a plot of Kaplan Meier survival curves. The difference in survival was significant in the Mantel-Cox log-rank test (P<0.0001).

As shown in FIG. 4, treatment with compound 1C resulted in survival rates of 80 to 100%. All mice treated with 40 µg of compound 1C were tumor free at Day 62. The median survival of the vehicle group was 21 days and the 40 µg compound 1C group displayed no mortality. All of the mice treated with compound D 1C that survived were re-challenged with a subcutaneous inoculation of MB49-luc cells in parallel with age-matched naïve controls on Day 62. The difference in survival was significant in the Mantel-Cox log-rank test (P<0.0001).

Figure 5:
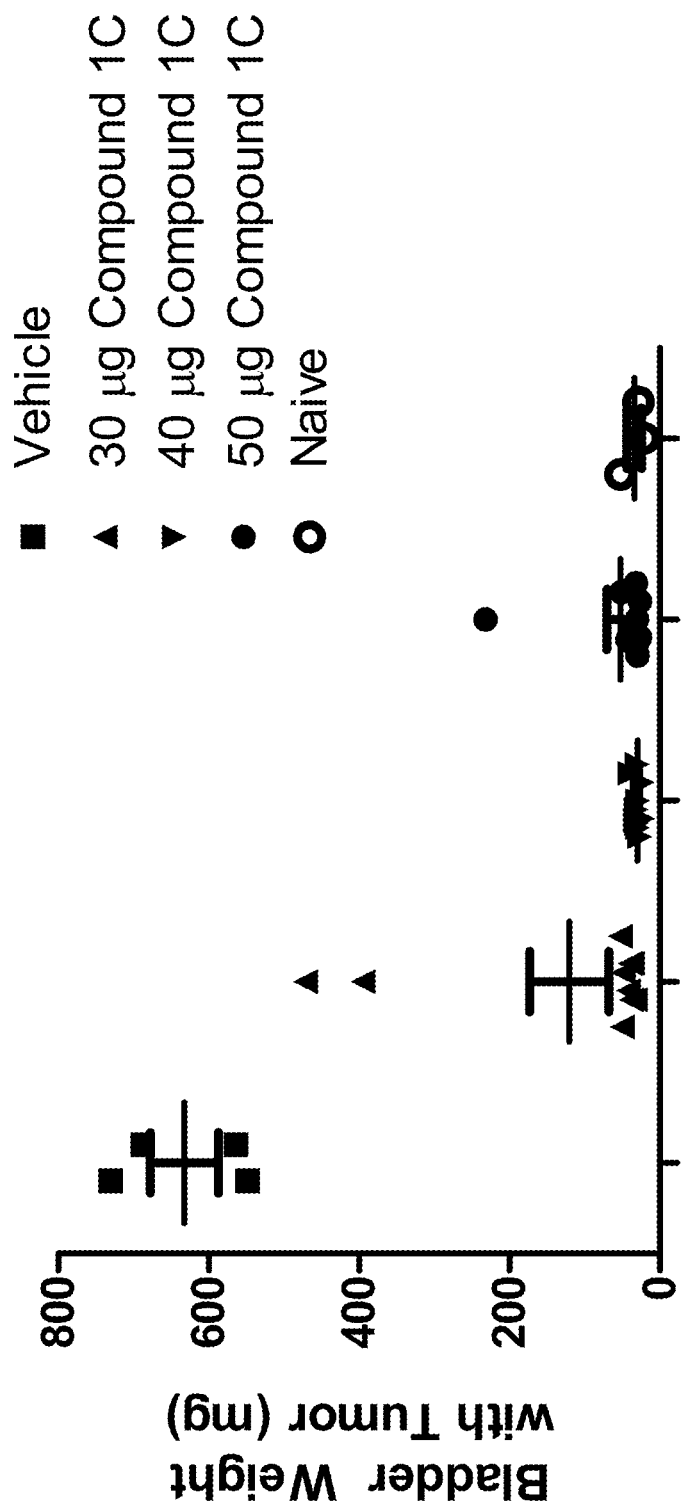
FIG. 5 is a scatterplot of bladder weights with tumors measured when animals exited the study or at the termination of the study.

At the termination of the study on Day 89, all animals were euthanized. Bladder weights were recorded and bladders were fixed in neutral buffered formalin for histology as shown in FIG. 5.

Figure 6:
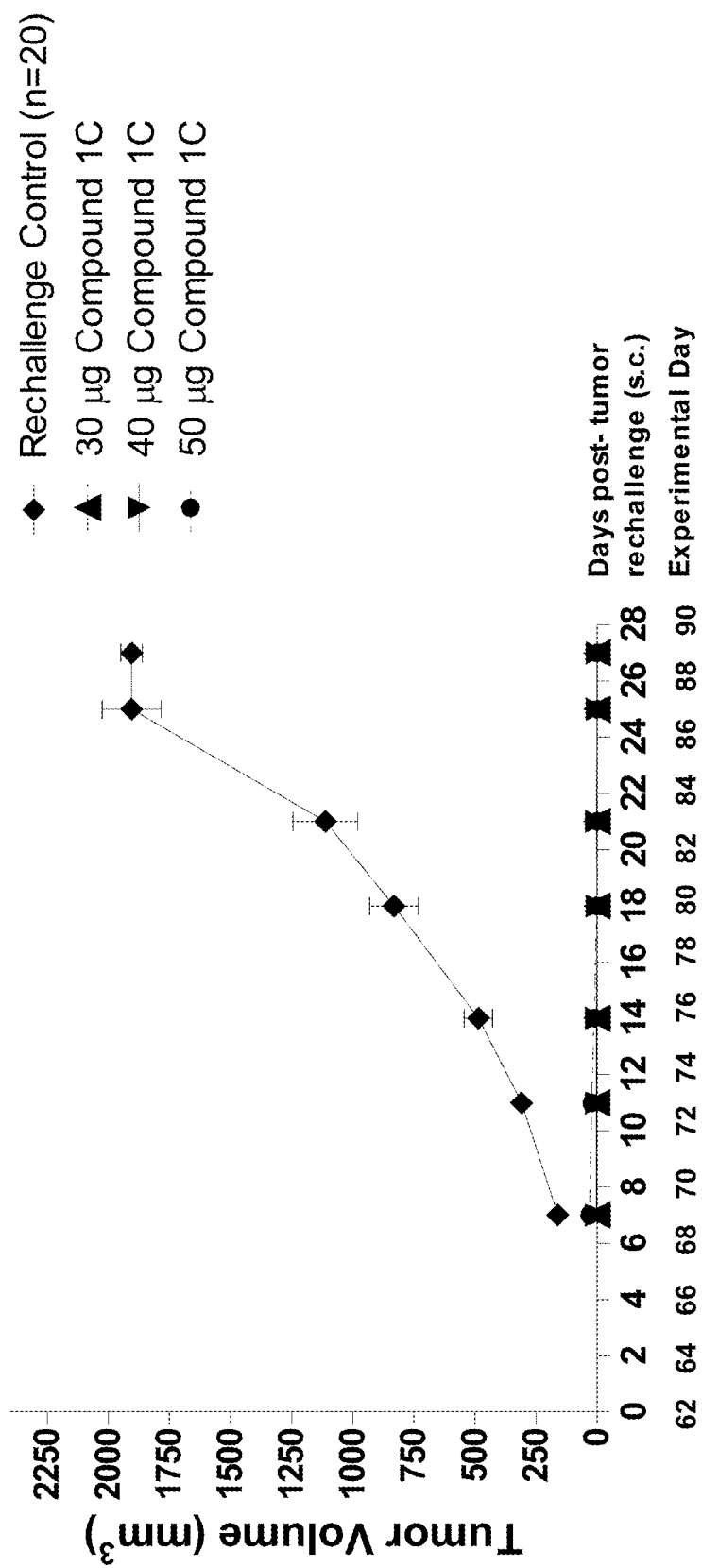
FIG. 6 is a graph of tumor weight versus time.

All of the mice treated with compound 1C that survived the initial challenge were re-challenged with a subcutaneous inoculation of MB49-luc cells in parallel with age-matched naïve controls on Day 62. The mice received no further treatment. The subcutaneous tumor growth data through experimental Day 89 are shown in FIG. 6. Subcutaneous tumors were measured with calipers. Volume in mm3=(a× b2) where a and b are the long and short diameters of the tumor, respectively. Data are presented as the mean±the SEM. By Day 89 all of the animals in the re-challenge control group were euthanized due to tumor burden. None of the animals treated with compound 1C in the initial challenge developed tumors in the re-challenge, demonstrating that compound 1C has the potential to induce a long lasting anti-tumor response through activation of immunological memory.

STING agonists induce antigen presentation to induce adaptive T cell responses. Specifically, STING agonists induce dendritic cell (DC) activation and maturation. Immature DC collect antigens throughout the body but live only a short time unless they receive a danger signal, through receptors for pathogen or damage associated molecular pattern receptors. STING agonism provides such as signal to induce DC activation and maturation. When this occurs, the DC upregulate expression of CD80 and CD86 (B7-1 and B7-2) which provide costimulation to T cells. The mature DC migrate to lymphoid organs such as lymph nodes and spleen, and the cells then can live for several weeks presenting antigen to T cells.

Figure 7:
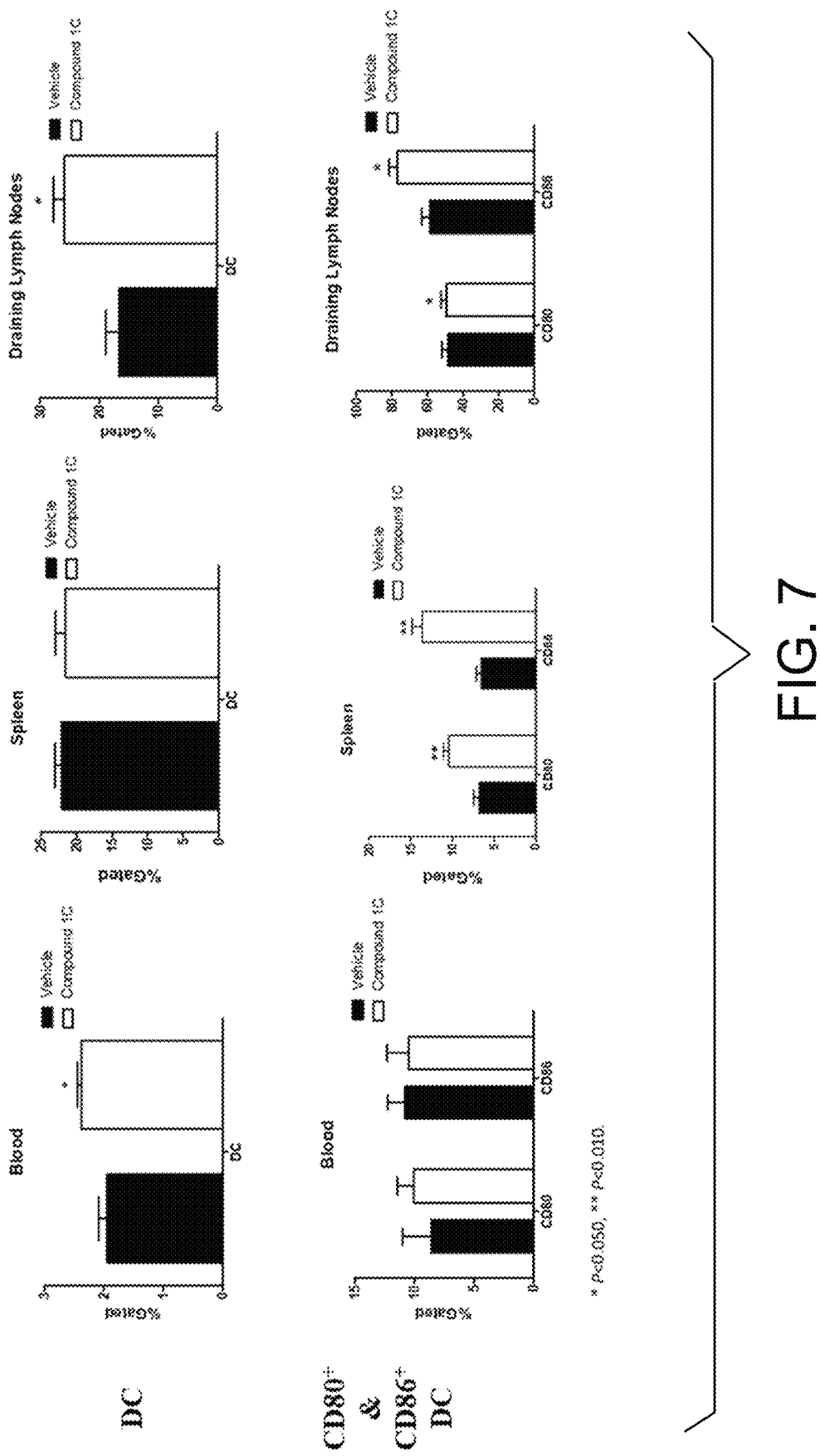
FIG. 7 depicts bar graphs showing dendritic cells in the blood, spleens and draining lymph nodes 24 hours after administration of compound 1C.

The effects on DC of a single dose of 40 μg compound 1C by bladder instillation in the mouse NMIBC model were examined. Compound 1C induced DC mobilization in the blood and draining lymph nodes, and significantly increased the proportion of activated DC as measured by CD80 and CD86 expression in the draining lymph nodes and spleen within 24 hours as shown in FIG. 7. Data are from 6 mice at each time point and are presented as the mean±the SEM. The increases in activated (CD80 and CD86 positive) DCs in the draining lymph nodes and spleen were statistically significant. The increases in the spleen demonstrate that compound 1C can induce systemic immune responses.

Figure 8:
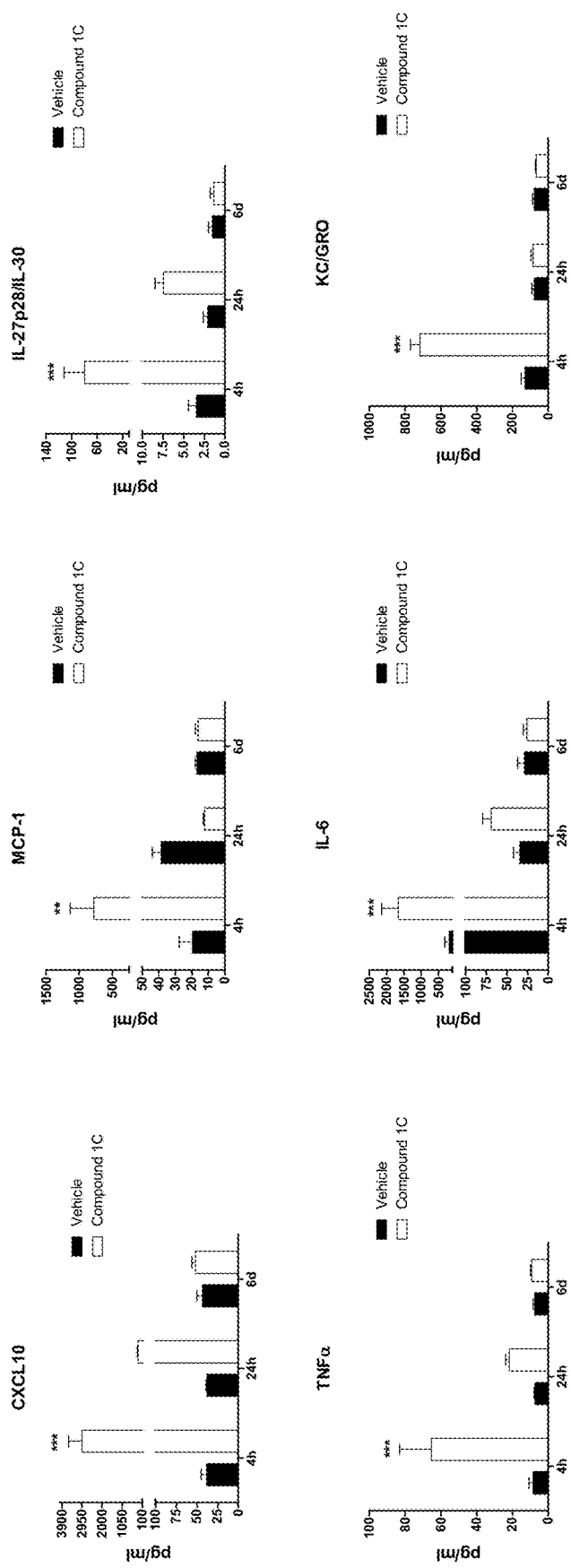
FIG. 8 depicts bar graphs showing serum cytokine levels 4 hours, 24 hours and 6 days post administration of compound 1C.

In the same study, measurement of serum cytokine and chemokine levels demonstrated the upregulation of Type I IFN induced responses such as CXCL10 and MCP-1, the antigen presenting cell cytokine IL-27 and pro-inflammatory cytokines at 4 hours and 24 hours after and 6 days in the NIMBC model (FIG. 8). Data are from 6 mice at each time point and are shown as the mean±the SEM.

Figure 9:
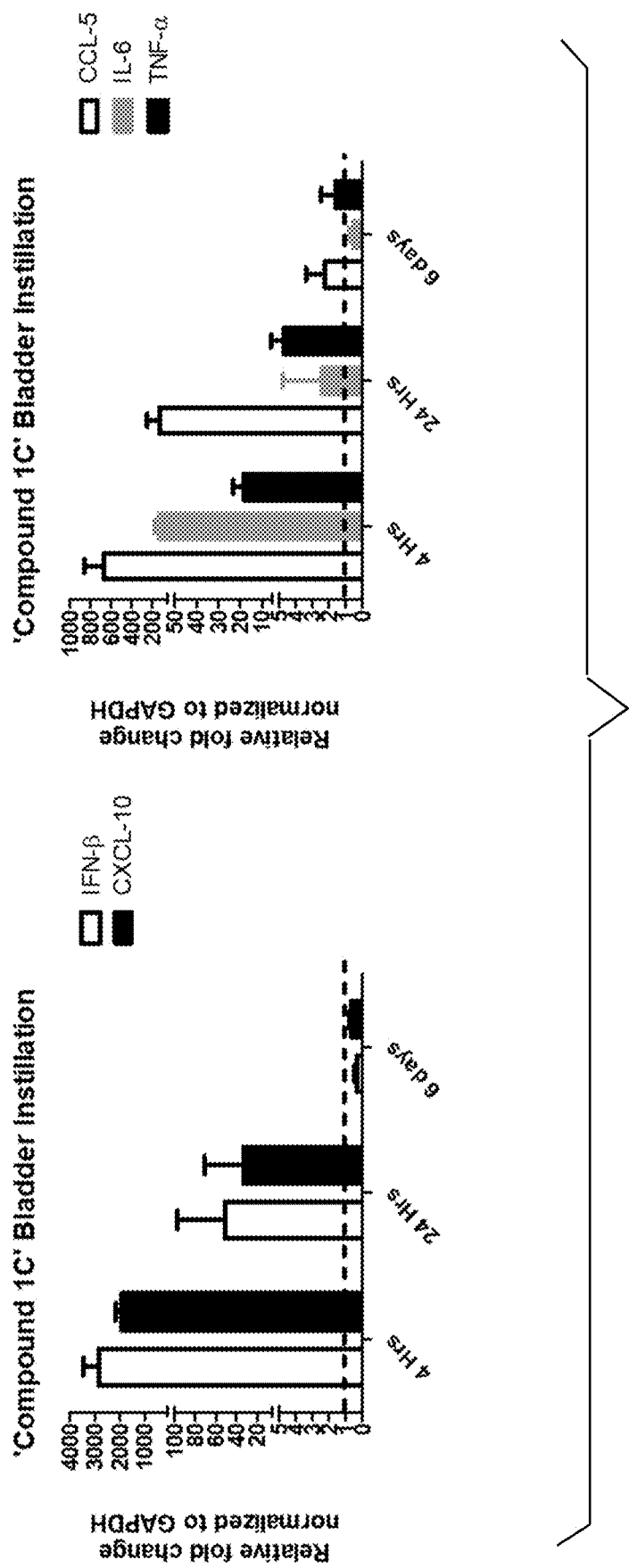
FIG. 9 depicts bar graphs showing message levels for cytokines and chemokines in bladder tissue at 4 hours, 24 hours and 6 days post administration of Compound 1C.

Analysis of bladder tissue mRNA from the mice after the treatment demonstrated the direct production of IFNβ, CXCL-10, CCL-5, IL-6 and TNFα. Message levels for cytokines and chemokines in bladder tissue at 4 hours, 24 hours and 6 days post administration of Compound 1C are shown in FIG. 9. The fold change relative to vehicle mice samples at each time point are shown. Data are from 6 mice at each time point and are shown as the mean±the SEM.

Figure 10:
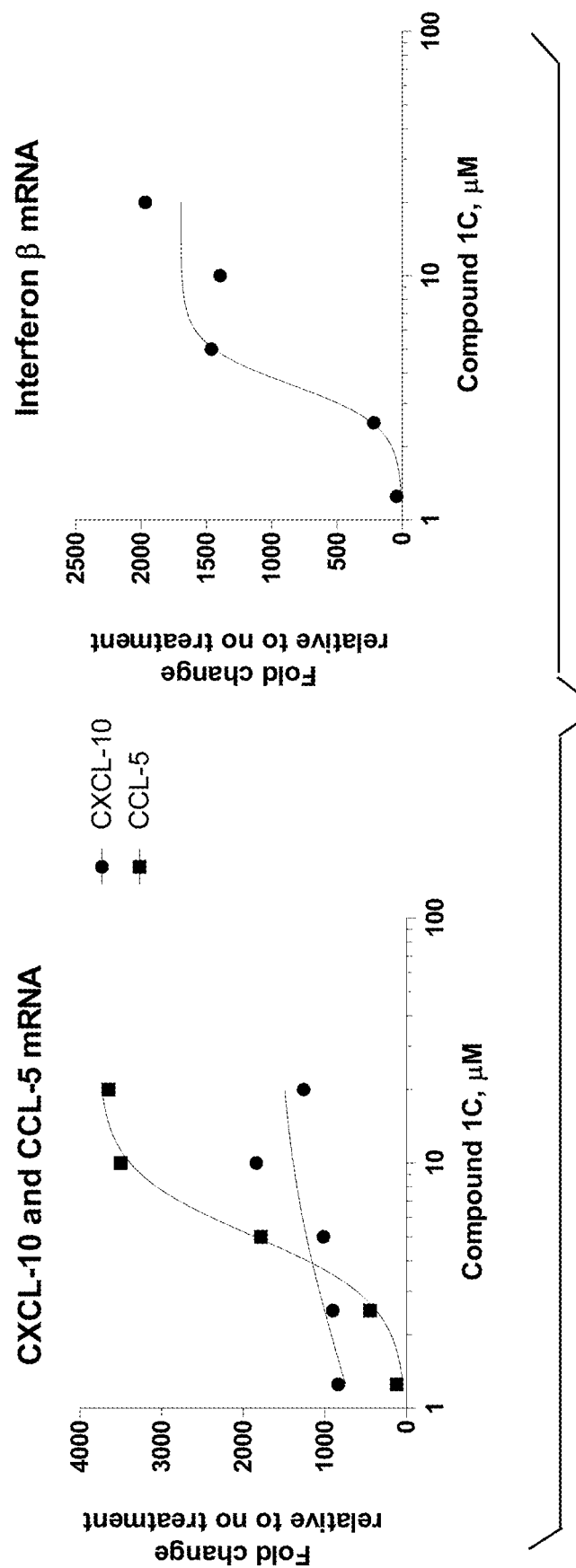
FIG. 10 depicts two graphs of change in expression of IFNβ and two Type I interferon-induced genes, CXCL-10 and CCL-5 as a function of dose of example 1C.

A similar induction of cytokine message was observed in human primary bladder epithelial cells. Human primary bladder cells were treated for 2 h with compound 1C over a range of concentrations to mimic clinical use, followed by fresh media without compound for an additional 6 h. Compound 1C increased IFNβexpression over 1000-fold within 2 h and expression of two Type I interferon-induced genes, CXCL-5 and CCL-5, was subsequently increased by over 1000-fold at the 6 h time after the treatment when cells were in fresh media (FIG. 10). These results suggest that the data from the in vivo mouse study will translate to the human setting.

Figure 11:
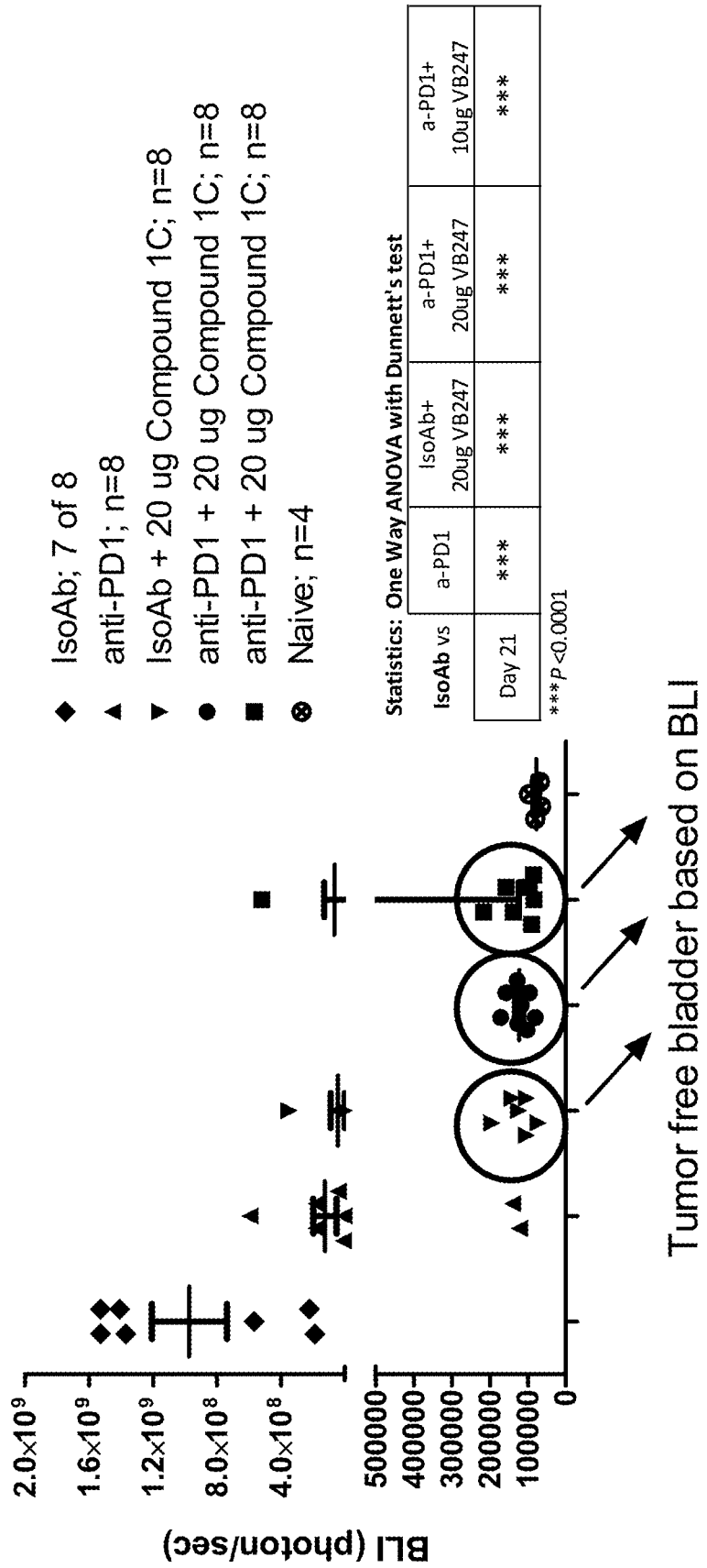
FIG. 11 is a scatterplot of BLI for various doses of anti-PD-1 antibody and compound 1C.

The efficacy of compound 1C in combination with anti-PD-1 checkpoint blockade was examined in the orthotopic NMIBC MB49-luc mouse model. Compound 1C was dosed by the intravesical route at 20 μg as a single agent and at 10 μg and 20 μg in combination with anti-PD-1 antibody (Mouse anti-CD279, clone RMP1-14) for a total of 3 weekly administrations. Anti-PD-1 antibody was dosed at 10 mg/kg by the intraperitoneal route every 4 days for a total of 5 doses. An equal amount of isotype control antibody (Rat IgG2a, clone 2A3) was dosed for mice receiving compound 1C as a single agent. Dosing was initiated on day 4 of the study. Treatment of mice with anti-PD-1 alone resulted in 2 out of 8 mice achieving complete responses by day 21 (FIG. 11). These data indicate that that the MB49luc orthotopic model may be considered a model of anti-PD-1 resistant NMIBC. Treatment with 20 μg compound 1C as a single agent resulted in 75% complete responses, whereas combination with anti-PD-1 improved the complete response rate to 100%. Furthermore, a dose of only 10 μg compound 1C in combination with anti-PD-1 resulted in 7 out of 8, or 87.5% complete responses (FIG. 11). These results indicate compound 1C can be combined with anti-PD-1 therapy to improve the efficacy of lower doses, achieving up to 100% complete responses similar to those achieved by higher doses as a single agent (FIG. 3).

MC-38 Tumor Bearing Mice Treated with Example 1C and Anti-PD-1 Eight week old female C57BL/6J mice were purchased from the Jackson Laboratory West (Sacramento, CA). During the study, the care and use of animals was conducted in accordance with the regulations of the Association for Assessment and Accreditation of Laboratory Animal Care (AAALAC). The protocol and any amendment (s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, NJ) were available ad libitum.

MC-38 cells were maintained in vitro as a monolayer culture in DMEM+10% heat-inactivated FBS and harvested at passage 5. Mice were inoculated subcutaneously with 1×106 MC-38 tumor cells in 100 μl phenol free DMEM on the lower right flank. Tumors were measured in two dimensions using calipers. Tumor volumes were calculated using the formula: volume (mm3)=(length×width2)/2. Animals were euthanized when the tumor volume reached 2000 mm3.

Tumors grew for 8 days to an average size of 150 mm3. Animals were randomized by tumor volume and body weight into groups of ten mice per treatment group on Day 0. Mice were treated by intra-tumoral injection of 5 μg of Example 1C in 30 μL of PBS or with PBS alone on Days 0, 3 and 7. Mice were treated with injections of 10 mg/kg anti-PD-1 antibody (Clone RMP1-14; Catalogue #BE0146) or an isotype control (Clone 2A3; Catalogue #BE0089) purchased from BioXcell (West Lebanon, NH) two times a week for three weeks. Tumor volumes (Tvol) were normalized to the initial tumor (Tinit) volume using the formula ((Tvol−Tinit)/(Tinit))*100. The study was terminated when the tumor size in the vehicle treated group reached 2,000 mm3. Animals with complete tumor regression were retained for a re-challenge study. The re-challenge study was initiated 21 days after complete tumor regression was observed.

All vehicle treated animals were alive until Day 17. By Day 30 complete regression of the tumors was observed in 7 out of 10 animals in the 5 µg Example 1C+anti-PD-1 treatment group, and 1 out of 10 animals in the 5 µg Example 1C monotherapy group. None of the anti-PD-1 monotherapy treated mice demonstrated complete regression of the tumors. Survival of the three groups from Day 0 through Day 34 is shown in Table 17.

TABLE 17

Number of surviving mice from Day 0 through Day 34 in the initial study.

| | Treatment | | | |
|---|---|---|---|---|
| Day | 10 mg/kg Isotype Control | 10 mg/kg Anti-PD-1 | 5 µg Example 1C | 5 µg Example 1C + 10 mg/kg Anti-PD-1 |
| 0 | 10/10 | 10/10 | 10/10 | 10/10 |
| 3 | 10/10 | 10/10 | 10/10 | 10/10 |
| 6 | 10/10 | 10/10 | 10/10 | 10/10 |
| 10 | 10/10 | 10/10 | 10/10 | 10/10 |
| 14 | 10/10 | 10/10 | 10/10 | 10/10 |
| 17 | 10/10 | 10/10 | 10/10 | 10/10 |
| 21 | 2/10 | 9/10 | 10/10 | 10/10 |
| 24 | 0/10 | 6/10 | 10/10 | 10/10 |
| 27 | 0/10 | 0/10 | 7/10 | 9/10 |
| 30 | 0/10 | 0/10 | 3/10 | 8/10 |
| 34 | 0/10 | 0/10 | 1/10 | 7/10 |

The 7 animals with complete regression of the initial tumors treated with 5 µg Example 1C and 10 mg/kg anti-PD-1 and one animal treated with Example 1C alone were re-challenged with MC-38 cells and a naïve control group was inoculated in parallel on Day 51 (re-challenge Day 0). No animals received any further treatment. By Day 14 of the re-challenge all naïve animals had measurable tumors. In the groups that were treated with Example 1C as a monotherapy or in combination with anti-PD-1 in the initial phase (8 animals from Table 14 above), 8 out of 8 animals showed no signs of tumor growth by re-challenge Day 14.

Treatment of MC-38 Tumors with Example 1C and Radiotherapy. Eight week old female C57BL/6J mice were purchased from the Jackson Laboratory West (Sacramento, CA). During the study, the care and use of animals was conducted in accordance with the regulations of the Association for Assessment and Accreditation of Laboratory Animal Care (AAALAC). The protocol and any amendment (s) or procedures involving the care and use of animals in this study was reviewed and approved by the Institutional Animal Care and Use Committee (IACUC) of Invivotek prior the initiation of the study. Mice were acclimated for 72 hours before inoculation. Mice were group housed (n=5/cage) and maintained on a 12 hour light and dark schedule. Reverse osmosis chlorinated water and irradiated food Purina rodent diet #5053 (Fisher Feeds, Bound Brook, NJ) were available ad libitum. MC-38 cells (murine colon adenocarcinoma) were maintained in vitro as a monolayer culture in DMEM+10% heat-inactivated FBS and harvested at passage 5. Mice were inoculated subcutaneously with 1×106 MC-38 tumor cells in 100 µl phenol free DMEM on the lower right flank. Tumors were measured in two dimensions using calipers. Tumor volumes were calculated using the formula: volume (mm3)=(length×width2)/2. Animals were euthanized when the tumor volume reached 2000 mm3. Tumors grew for 7 days to an average size of 100 mm3. Animals were randomized by tumor volume and body weight into groups of ten mice per treatment group on Day −2. On Days −2, −1 and 0 received 5 Gy of radiation targeted to the tumor using the Small Animal Radiation Research Platform (SARRP) manufactured by Xstrahl Inc. Radiotherapy treatments were given according to the outline in Table 18. Mice were treated by intra-tumoral injection of 5 µg of Example 1C in 30 µL of PBS or with PBS alone on Days 0, 3, 7 and 14. Radiotherapy treatments were given according to the outline in Table 19.

TABLE 19

Example R Experimental Design

| Group | Animals/ group | Day −2 RT | Day −1 RT | Day 0 RT (before Example C) | IT Example 1C (5 µg/ 30 µl) | IT Vehicle |
|---|---|---|---|---|---|---|
| 1 | 10 | 5 Gy | 5 Gy | 5 Gy | Day 0, 3, 7, 14 | N/A |
| 2 | 10 | N/A | 5 Gy | 5 Gy | Day 0, 3, 7, 14 | N/A |
| 3 | 10 | N/A | N/A | N/A | Day 0, 3, 7, 14 | N/A |
| 4 | 10 | 5 Gy | 5 Gy | 5 Gy | N/A | N/A |
| 5 | 10 | N/A | N/A | N/A | | Day 0, 3, 7, 14 |

The last vehicle treated animals were alive until Day 26. The re-challenge study was initiated 39 days after complete tumor regression was observed. The results of animals with complete tumor regression following the primary challenge and were tumor free after the re-challenge are shown in Table 20.

TABLE 20

Tumor free mice following the primary and re-challenge

| Group | Animals/ Group | Treatment | #Tumor Free Mice after Treatment/ #Tumor Free Mice after Re-challenge |
|---|---|---|---|
| 1 | 10 | RT Day −2, −1, 0/Example 1C IT Day 0, 3, 7, 14 | 8/7 |
| 2 | 10 | RT Day −1, 0/Example 1C IT Day 0, 3, 7, 14 | 4/3 |
| 3 | 10 | Example 1C IT Day 0, 3, 7, 14 | 0/0 |
| 4 | 10 | RT Day −2, −1, 0 | 0/0 |
| 5 | 10 | Vehicle IT Day 0, 3, 7, 14 | 0/0 |

Figure 12:
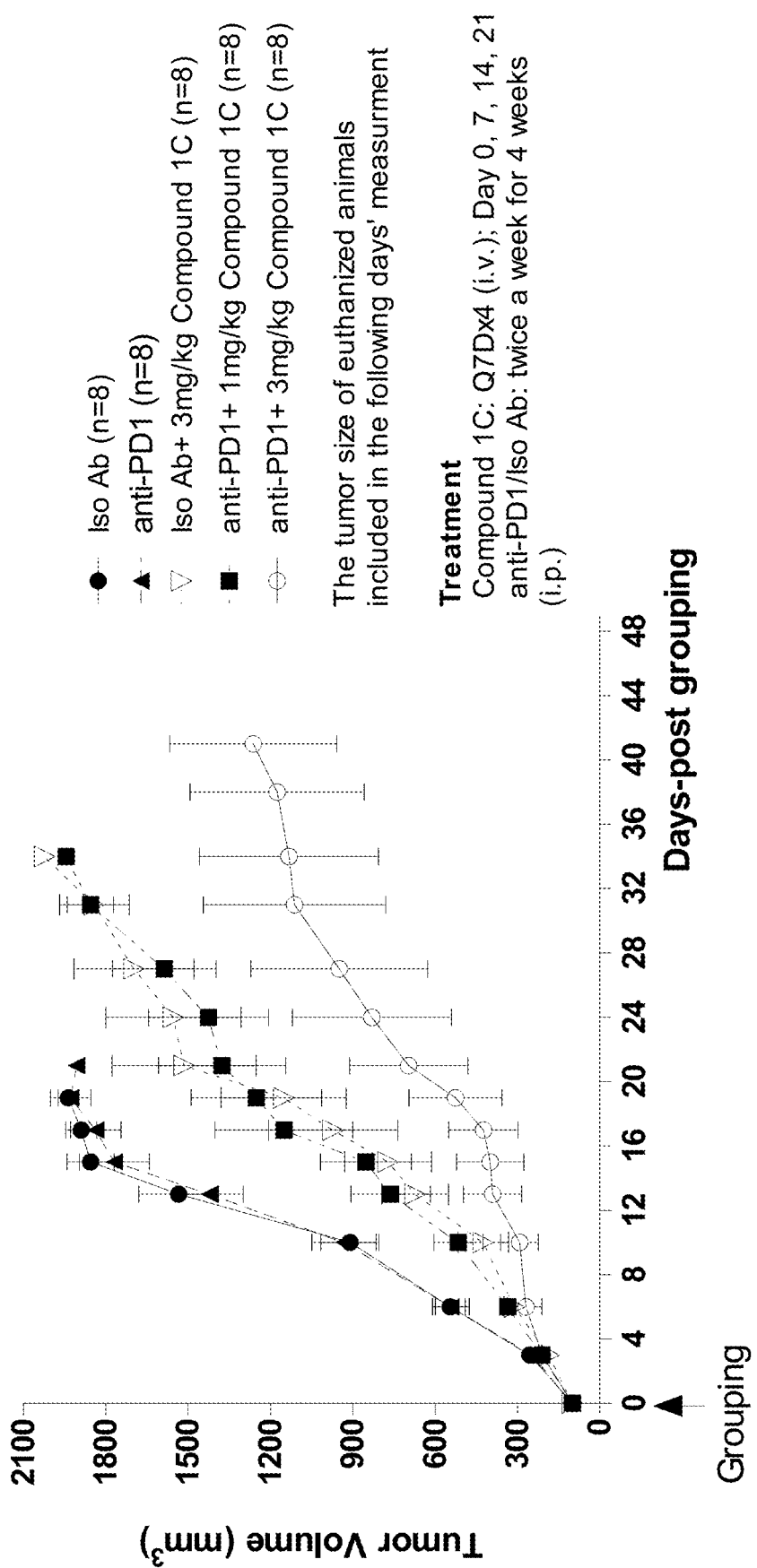
FIG. 12 is a graph of tumor size versus time for various doses of anti-PD-1 antibody and compound 1C in the subcutaneous CT26 colon tumor model.
Figure 13:
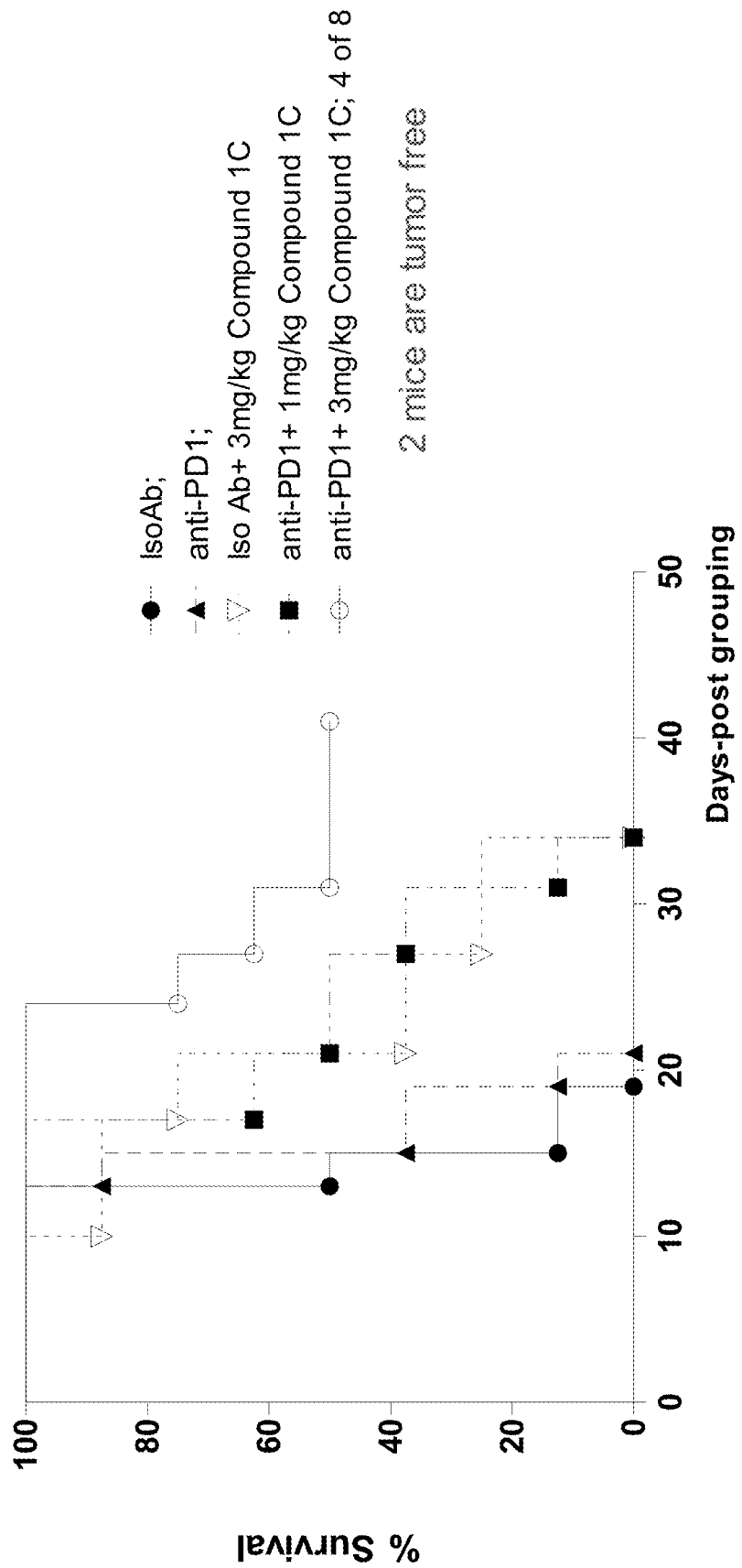
FIG. 13 is a graph of percent survival versus time for various doses of anti-PD-1 antibody and compound 1C in the subcutaneous CT26 colon tumor model.

The utility of compound 1 in treating solid tumors, such as colon carcinoma, was demonstrated as shown below. In this case, compound 1C was administered in parenteral solution intravenously, rather than intravesically. Compound 1C was found to achieve substantial efficacy by systemic administration, as demonstrated in the syngeneic CT26 subcutaneous colon tumor model with intravenous dosing. In this model treatment with anti-PD1 antibody (Mouse anti-CD279, clone RMP1-14) alone did not result in tumor growth inhibition (FIG. 12) or increased duration of survival (FIG. 13), demonstrating that this model is highly resistant to anti-PD1 therapy as a single agent. By contrast, four weekly doses of 3 mg/kg compound 1C by the intravenous (IV) route resulted in substantial tumor growth inhibition and increased survival time (FIGS. 12 and 13). The combination of four weekly doses of 3 mg/kg compound 1C by the intravenous (IV) route with anti-PD-1 antibody therapy resulted in further efficacy as shown by increased tumor growth inhibition and increased survival (FIGS. 12 and 13). The efficacy of 1 mg/kg compound 1C in combination with anti-PD1 antibody therapy was similar to that of 3 mg/kg of compound 1C as a single agent.

Figure 14:
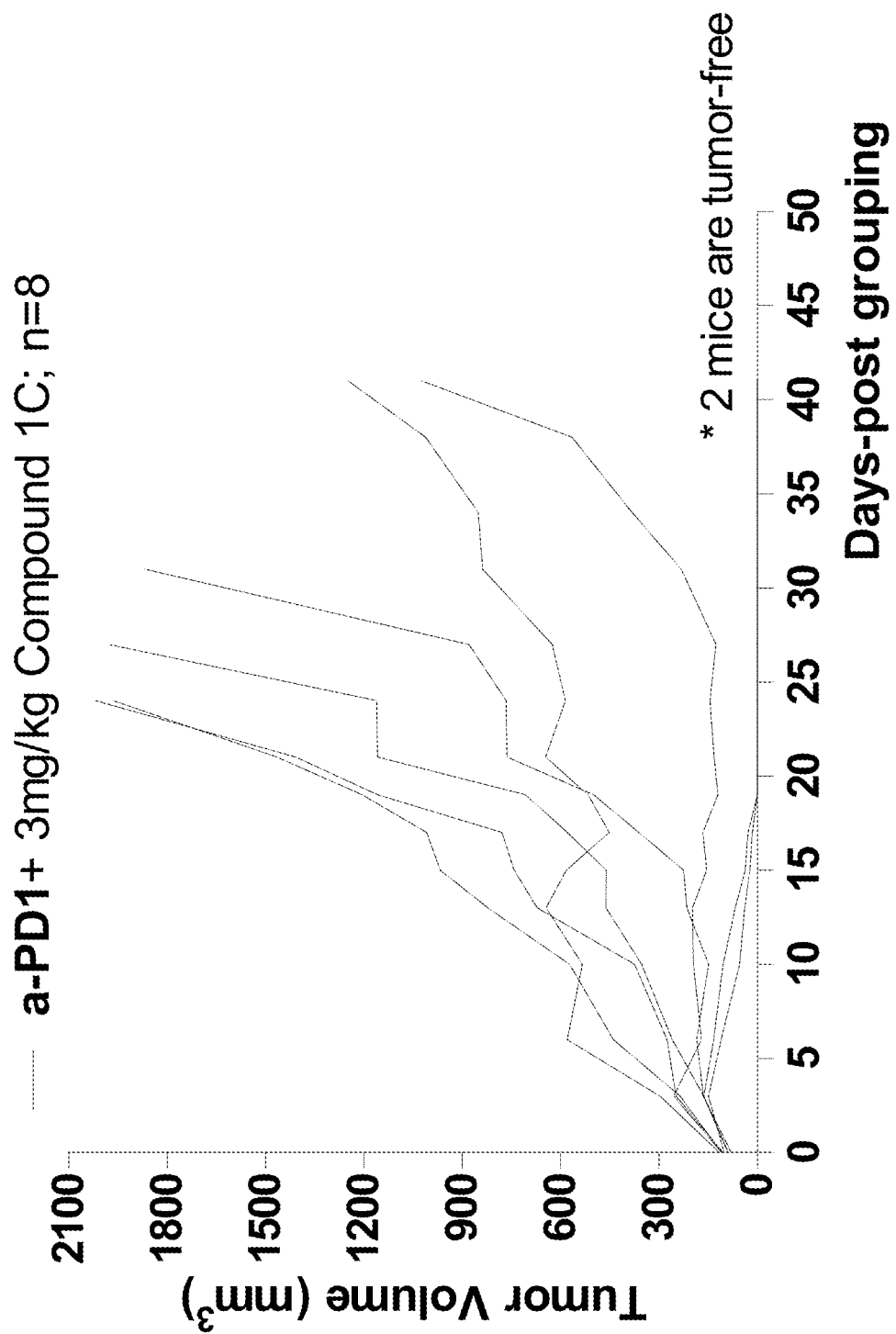
FIG. 14 is a graph of tumor size versus time for anti-PD-1 antibody and compound 1C.

Very importantly 2 out of 8 or 25% complete regressions were achieved after 3 weekly IV treatments with compound 1C (FIG. 14). In addition to the two complete regressions, an additional mouse displayed little tumor progression throughout the 31 days of the study so far. FIG. 14 shows individual tumor growth kinetics for mice receiving 3 mg/kg compound 1C in combination with anti-PD-1 antibody. These data demonstrate that compound 1C can achieve substantial efficacy including complete responses by systemic administration.

Chemistry

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise.

Abbreviations as used herein, are defined as follows: Ac=acetyl; AcCl=acetyl chloride; Ac2O=acetic anhydride; ACN=acetonitrile; AcOH=acetic acid; AIBN=Azobisisobutyronitrile; app=apparent; aq.=aqueous; Avi=peptide sequence allowing biotinylation by the enzyme BirA; BLI=bioluminescence imaging; Bn=benzyl; brine=saturated aqueous sodium chloride; BSA (chemistry)= N,O-bis(trimethylsilyl)acetamide; BSA (biology)=bovine serum albumin; br=broad; t-BuOH=tert-butyl alcohol; Bu2SnO=Dibutyltin(IV) oxide; Bz=benzoyl; comp=complex multiplet (non-magnetically equivalent overlapping signals); d=doublet; DBU=1,8-Diazabicyclo[5.4.0]undec-7-ene; DCA=dichloroacetic acid; DCM=dichloromethane; dd=doublet of doublets; ddd=doublet of doublets of doublets; DDTT=(E)-N,N-dimethyl-N'-(3-thioxo-3H-1,2,4-dithiazol-5-yl)formimidamide; dq=doublet of quartets; dt=doublet of triplets; (DHQ)2Pyr=Hydroquinine 2,5-diphenyl-4,6-pyrimidinediyl diether; DIEA=diisopropylethylamine; DMA=dimethylacetamide; DMAP=4-N,N-dimethylaminopyridine; DIEA=N,N-diisopropylethylamine; DMOCP=2-chloro-5,5-dimethyl-1,3,2-dioxaphosphorinane 2-oxide; DMSO=dimethylsulfoxide; DMTr=4,4'-dimethoxytriphenylmethyl; DMTrCl=4,4'-dimethoxytriphenylmethyl chloride; EA=EtOAc=ethyl acetate; EtOH=ethanol; Et3N=triethylamine; eq=Equivalents; GAPDH=Glyceraldehyde 3-phosphate dehydrogenase; HCl=hydrochloric acid; HEK=human embryonic kidney cell line; hept=heptet; HIS=polyhistidine-tag; HPLC=high performance liquid chromatography; hr=hour; hrs=hours; LCMS=liquid chromatography-mass spectrometry; m=multiplet; MeNH2=methylamine; MeOH=methanol; MeONa=sodium methoxide; min=minutes; HPLC=medium pressure liquid chromatography; MS=molecular sieves; NaOAc=sodium acetate; MPLC=medium pressure liquid chromatography; NP-HPLC=normal phase medium pressure liquid chromatography; PBS=phosphate buffered saline; PBMC=human peripheral blood mononuclear cells; PE=petroleum ether; PG=protecting group; PVDF Membrane=polyvinylidene difluoride membrane; PVT=polyvinyltoluene; prep. RP-HPLC=preparative reverse phase HPLC; Py=pyridine; Py·TFA=pyridinium trifluoroacetate; quant=quantitative yield; q=quartet; RAW=murine macrophage cancer cell line; RP=reverse phase; RT=room temperature; s=singlet; sat.=saturated; SDS-PAGE=sodium dodecyl sulfate polyacrylamide gel electrophoresis; SEAP=secreted alkaline phosphatase; SPA=scintillation proximity assay; SUMO=small ubiquitin-like modifier tag; t=tertiary; TBAF=tetrabutylammonium fluoride; TBDPS=tert-butyldiphenylsilyl; TBDPSCl=tert-butyldiphenylsilyl chloride; TBSCl=tert-butyldimethylsilyl chloride; TBS=tert-butyldimethylsilyl; TEA=triethylamine; TES=triethylsilane, TFA=trifluoroacetic acid; THF=tetrahydrofuran; THP1=Tohoku-Hospital Pediatrics-1 human monocytic cell line derived from an acute monocytic leukemia patient; TMSCl=chlorotrimethylsilane; TMSOTf=Trimethylsilyl trifluoromethanesulfonate; TR=retention time (minutes); and Tris=tris(hydroxymethyl)aminomethane.

Names of compounds as used herein, were generated as follows: Names for linear intermediates were created using Chemdraw (CambridgeSoft) version 12.0.2. These names were generated using the "Convert Structure to Name" functionality found in the "Structure" menu. Names for all macrocyclic intermediates and final compounds were generated using MarvinSketch (Chemaxon Ltd.) version 18.22. These names were generated by using the "Preferred IUPAC Name" option in the "Generate Name . . . " utility found in the "Structure" menu.

Compounds were analyzed on an Acquity Ultra Performance Liquid Chromatography system employing an Acquity UPLC BEH C18, 1.7 μm, 2.1×50 mm column. Detection was via an Aquity Ultra Performance LC PDA detector and an Acquity SQD single quadrupole mass spectrometer using $H_2O$+0.1% formic acid (A) and ACN+0.1% formic acid (B) as eluents. Unless specified elsewhere, Method A was used for all LCMS analyses.

Method A—Gradient: 0-0.1 min—Isocratic—10% B; 0.1-1.3 min—Linear gradient 10%-90% B; 1.3-1.8 min—Isocratic 90% B. Flow rate: 0.6 mL/min.

Method B—Gradient: 0-0.1 min—Isocratic—1% B; 0.1-1.3 min—Linear gradient 1%-50% B; 1.3-1.8 min—Isocratic 50% B. Flow rate: 0.6 mL/min.

Method C—Gradient: 0-0.1 min—Isocratic—0.5% B; 0.1-1.3 min—Linear gradient 0.5%-50% B; 1.3-1.8 min—Isocratic 50% B. Flow rate: 0.6 mL/min.

Method D—Gradient: 0-0.1 min—Isocratic—100% A; 0.1-1.5 min—Linear gradient 0%-20% B; 1.5-2.0 min—Isocratic 20% B. Flow rate: 0.6 mL/min.

Method E—Gradient: 0-0.1 min—Isocratic—40% B; 0.1-1.3 min—Linear gradient 40%-95% B; 1.3-1.8 min—Isocratic 95% B. Flow rate: 0.6 mL/min.

NMR Spectroscopy Method: 1H NMR (400 MHz); 19F NMR (376 MHz), run in decoupled mode; and 31P NMR (162 MHz), run in decoupled mode; Spectroscopy was conducted on a Bruker 400 MHz Avance II FTNMR Spectrometer. 1H NMR chemical shifts (δ) are reported in parts per million (ppm) and referenced to the residual C—H signal from the deuterated solvent indicated.

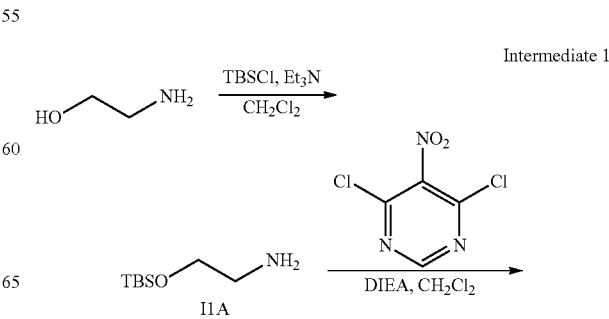

Intermediate 1

-continued

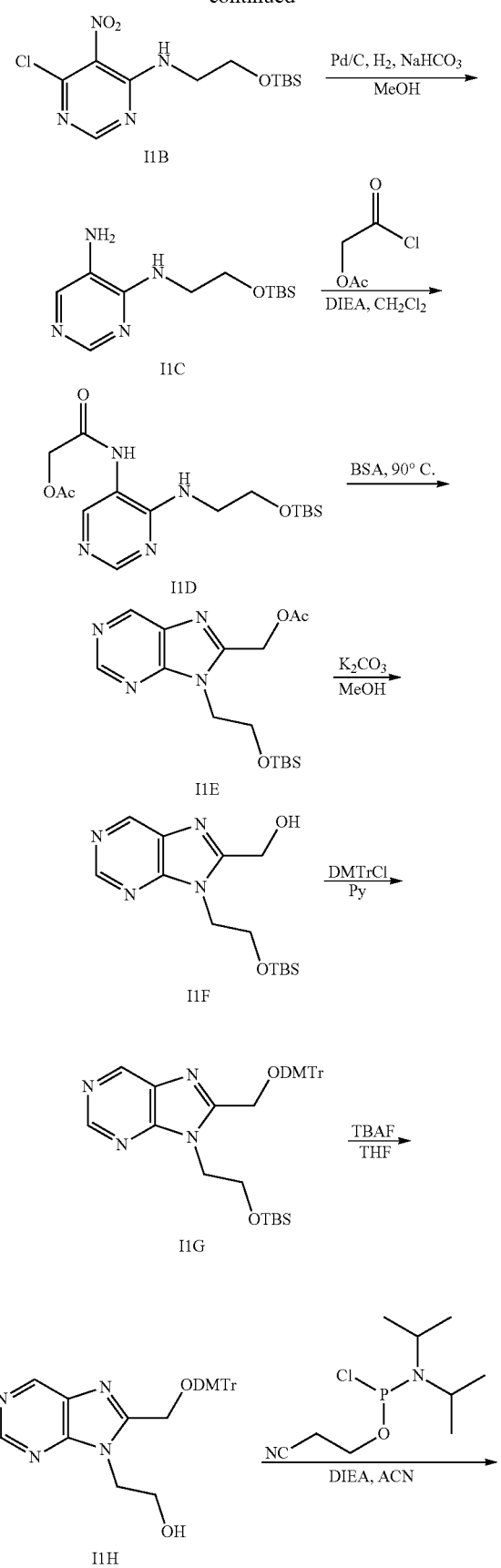

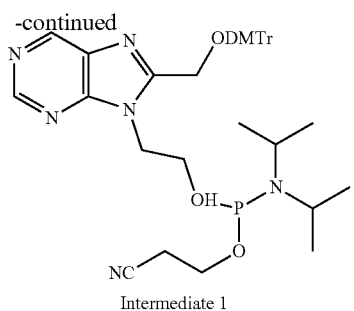

Intermediate 1

2-((tert-Butyldimethylsilyl)oxy)ethanamine (I1A)

To a solution of 2-aminoethanol (2.50 g, 40.9 mmol) in DCM (50 mL) was added Et$_3$N (6.30 mL, 45.20 mmol) followed by a solution of TBSCl (6.20 g, 41.1 mmol) in DCM (20 mL) at RT over 10 minutes. The reaction mixture was stirred at RT for 4 hrs, whereupon it was diluted with DCM and washed with saturated, aq. NaHCO$_3$, then brine. The organic layer was dried (Na$_2$SO$_4$) and then concentrated under reduced pressure to give I1A (6.86 g, 96%) as a clear, colorless oil. $^1$H NMR (CDCl$_3$) δ 3.60 (t, J=5.3 Hz, 2H), 2.74 (t, J=5.3 Hz, 2H), 0.88 (s, 9H), 0.05 (s, 6H).

N-(2-((tert-Butyldimethylsilyl)oxy)ethyl)-6-chloro-5-nitropyrimidin-4-amine (I1B)

To a solution of 4,6-dichloro-5-nitropyrimidine (7.59 g, 39.1 mmol) in DCM (150 mL) cooled to −78° C. was added DIEA (6.00 mL, 43.1 mmol) followed by I1A (6.86 g, 39.1 mmol) as a solution in DCM (50 mL) over 1 hr. The reaction mixture was stirred at −78° C. for 5 hrs, then at RT overnight. The resulting solution was diluted with DCM, and then washed with sat. aq. NaHCO$_3$, water, and brine. The organic layer was dried (MgSO$_4$) and then concentrated under reduced pressure. The residue was purified by silica gel chromatography (0-10% MeOH/DCM) to give I1B (9.92 g, 76%) as a pale yellow oil. LCMS m/z 333.1 (M+H)$^+$. $^1$H NMR (CDCl$_3$) δ 8.36 (s, 1H), 7.88 (br s, 1H), 3.81-3.78 (m, 2H), 3.74-3.70 (m, 2H), 0.89 (s, 9H), 0.06 (s, 6H).

N4-(2-((tert-Butyldimethylsilyl)oxy)ethyl)pyrimidine-4,5-diamine (I1C)

A mixture of I1B (1.00 g, 3.00 mmol), 10% Pd/C (200 mg), and NaHCO$_3$ (505 mg, 6.01 mmol) in MeOH (50 mL) was hydrogenated at 50 psi H$_2$ overnight using a Parr shaker. The reaction mixture was filtered through a pad of Celite® and the filtrate was concentrated under reduced pressure. The residue was partitioned between EtOAc and H$_2$O. The organic layer was removed and washed with sat. aq. NH$_4$Cl, H$_2$O, and then brine. The organic layer was dried (MgSO$_4$) and then concentrated under reduced pressure. The residue was purified by silica gel chromatography (0-10% MeOH/DCM) to give I1C (722 mg, 90%) as a light tan solid. LCMS m/z 269.2 (M+H)$^+$. $^1$H NMR (CDCl$_3$) δ 8.20 (s, 1H), 7.67 (s, 1H), 5.45 (br s, 1H), 3.75 (t, J=5.0 Hz, 2H), 3.55 (t, J=5.0 Hz, 2H), 3.23 (br s, 2H), 0.83 (s, 9H), −0.01 (s, 6H).

2-((4-((2-((tert-Butyldimethylsilyl)oxy)ethyl)amino)pyrimidin-5-yl)amino)-2-oxoethyl acetate (I1D)

To a solution of I1C (722 mg, 2.69 mmol) in DCM (15 mL) was added DIEA (609 μL, 3.50 mmol), and the resulting mixture was cooled to 0° C. 2-Chloro-2-oxoethyl acetate (304 μL, 2.83 mmol) was added in a dropwise fashion. The resulting mixture was stirred at 0° C. for 1 hr, then allowed to warm to RT and stirred overnight. The reaction mixture was diluted with DCM, and washed with sat. aq. NaHCO$_3$, H$_2$O, and brine. The organic layer was dried (MgSO$_4$), and then concentrated under reduced pressure to give I1D (901 mg, 91%) as a pale yellow oil. LCMS m/z 369.3 (M+H)+. $^1$H NMR (CDCl$_3$) δ 8.43 (s, 1H), 8.30 (br s, 1H), 8.05 (s, 1H), 5.73 (br t, J=5.0 Hz, 1H), 4.68 (s, 2H), 3.74 (t, J=5.5 Hz, 2H), 3.57 (dt, J=5.5, 5.0 Hz, 2H), 2.15 (s, 3H), 0.85 (s, 9H), 0.02 (s, 6H).

(9-(2-((tert-Butyldimethylsilyl)oxy)ethyl)-9H-purin-8-yl)methyl acetate (I1E)

A mixture of I1D (901 mg, 2.45 mmol) and BSA (10 mL) was heated at 90° C. for 4 hrs, and then cooled to RT. The reaction mixture was diluted with DCM, and washed with sat. aq. NaHCO3, H2O, and brine. The organic layer was dried over MgSO4, and then filtered. To the filtrate was added silica gel (10 g), and then the mixture was concentrated under reduced pressure. The preadsorbed material was purified by silica gel chromatography (0-1.5% MeOH/DCM) to give I1E (740 mg, 86%) as a pale yellow solid. LCMS m/z 351.2 (M+H)+. 1H NMR (CDCl3) □□8.89 (s, 1H), 8.75 (s, 1H), 5.28 (s, 2H), 4.31 (t, J=5.1 Hz, 2H), 3.78 (t, J=5.1 Hz, 2H), 1.96 (s, 3H), 0.54 (s, 9H), −0.37 (s, 6H).

(9-(2-((tert-Butyldimethylsilyl)oxy)ethyl)-9H-purin-8-yl)methanol (I1F)

A mixture of I1E (1.20 g, 3.42 mmol) and K2CO3 (47.0 mg, 0.340 mmol) in MeOH (60 mL) was stirred at RT overnight, and then concentrated under reduced pressure. The residue was partitioned between EtOAc and H2O. The organic layer was removed and the aqueous layer was extracted with EtOAc (2×). The combined organic layers were washed with brine, dried (MgSO4), and then concentrated under reduced pressure to give I1F (1.01 g, 95%) of sufficient purity for subsequent transformations. LCMS m/z 308.2 (M+H)+. 1H NMR (CDCl3) □□9.01 (s, 1H), 8.89 (s, 1H), 4.99 (s, 2H), 4.75 (br s, 1H), 4.47 (t, J=5.0 Hz, 2H), 3.98 (t, J=5.0 Hz, 2H), 0.70 (s, 9H), −0.20 (s, 6H).

8-((Bis(4-methoxyphenyl)(phenyl)methoxy)methyl)-9-(2-((tert-butyldimethylsilyl)oxy)ethyl)-9H-purine (I1G)

A mixture of I1F (1.01 g, 3.27 mmol) and DMTrCl (1.33 g, 3.93 mmol) in pyridine (11 mL) was stirred at RT overnight. The resulting mixture was concentrated under reduced pressure, and then the residue was redissolved in DCM (20 mL). Silica gel (5 g) was added, and the mixture was concentrated to dryness under reduced pressure. The residue was purified by silica gel chromatography (0-10% MeOH/DCM) to give I1G (2.05 g, quant) as a white solid. LCMS m/z 610.3 (M+H)+. $^1$H NMR (CDCl$_3$) δ 9.06 (s, 1H), 8.92 (s, 1H), 7.48-7.14 (comp, 9H), 6.83 (d, J=8.8 Hz, 4H), 4.50 (s, 2H), 4.35 (t, J=5.4 Hz, 2H), 3.78-3.75 (comp, 8H), 0.57 (s, 9H), −0.39 (s, 6H).

2-(8-((Bis(4-methoxyphenyl)(phenyl)methoxy)methyl)-9H-purin-9-yl)ethanol (I1H)

To a solution of I1G (2.10 g, 3.44 mmol) in THF (20 mL) cooled to −5° C. was added TBAF/THF (1 M, 4.40 mL, 4.40 mmol) in a slow, dropwise fashion. The reaction mixture was stirred at 0° C. for 1.5 hrs, whereupon silica gel (5 g) was added. The resulting mixture was concentrated under reduced pressure, and then purified by silica gel chromatography (0-10% MeOH/DCM) to give I1H (1.29 g, 77%) as a white solid. LCMS m/z 497.3 (M+H)+. $^1$H NMR (CDCl$_3$) δ 9.09 (s, 1H), 8.92 (s, 1H), 7.47-7.23 (comp, 9H), 6.85 (d, J=9.0 Hz, 4H), 4.49 (s, 2H), 4.26 (t, J=4.8 Hz, 2H), 3.88 (dt, J=5.6, 4.8 Hz, 2H), 3.78 (s, 6H), 3.38 (br t, J=5.6 Hz, 1H).

2-(8-((Bis(4-methoxyphenyl)(phenyl)methoxy)methyl)-9H-purin-9-yl)ethyl (2-cyanoethyl) diisopropylphosphoramidite (Intermediate 1)

To a solution of I1H (1.29 g, 2.60 mmol) in ACN (13 mL) was added DIEA (1.36 mL, 7.81 mmol) followed by dropwise addition of neat 3-((chloro(diisopropylamino)phosphino)oxy)propanenitrile (0.78 mL, 3.12 mmol). The reaction mixture was stirred at RT for 2 hrs, and then quenched by the addition of 5% aq. NaHCO$_3$(1 mL). The resulting mixture was stirred for 10 min, and then partially concentrated under reduced pressure. The remaining solution was purified directly by RP-MPLC (5-100% ACN/H$_2$O containing 0.04% NH$_4$HCO$_3$) to give Intermediate 1 (1.40 g, 77%) as a white foam. LCMS m/z 614.3 (M+H+OH—N,N-diisopropylamino)+. $^1$H NMR (CDCl$_3$) δ 9.05 (s, 1H), 8.92 (s, 1H), 7.47-7.19 (comp, 5H), 7.37 (d, J=9.0 Hz, 4H), 6.83 (d, J=9.0 Hz, 4H), 4.55 (d, J=11.8 Hz, 1H), 4.50 (d, J=11.8 Hz, 1H), 4.47-4.44 (comp, 2H), 3.86-3.72 (comp, 2H), 3.76 (s, 6H), 3.48-3.43 (comp, 2H), 3.33-3.24 (comp, 2H), 2.38 (t, J=6.3 Hz, 2H), 1.01 (d, J=6.8 Hz, 6H), 0.84 (d, J=6.8 Hz, 6H). $^{31}$P NMR (CDCl$_3$) δ 148.1.

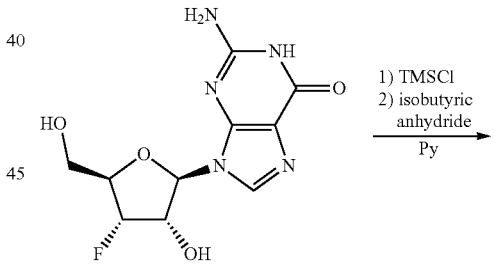

Intermediate 2

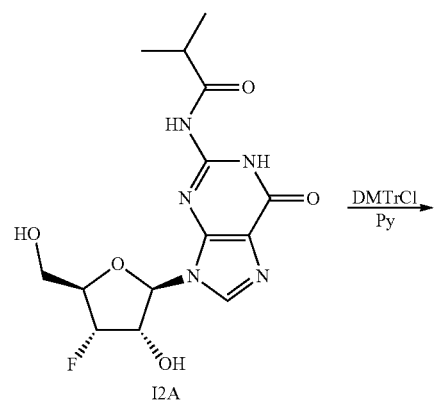

I2A

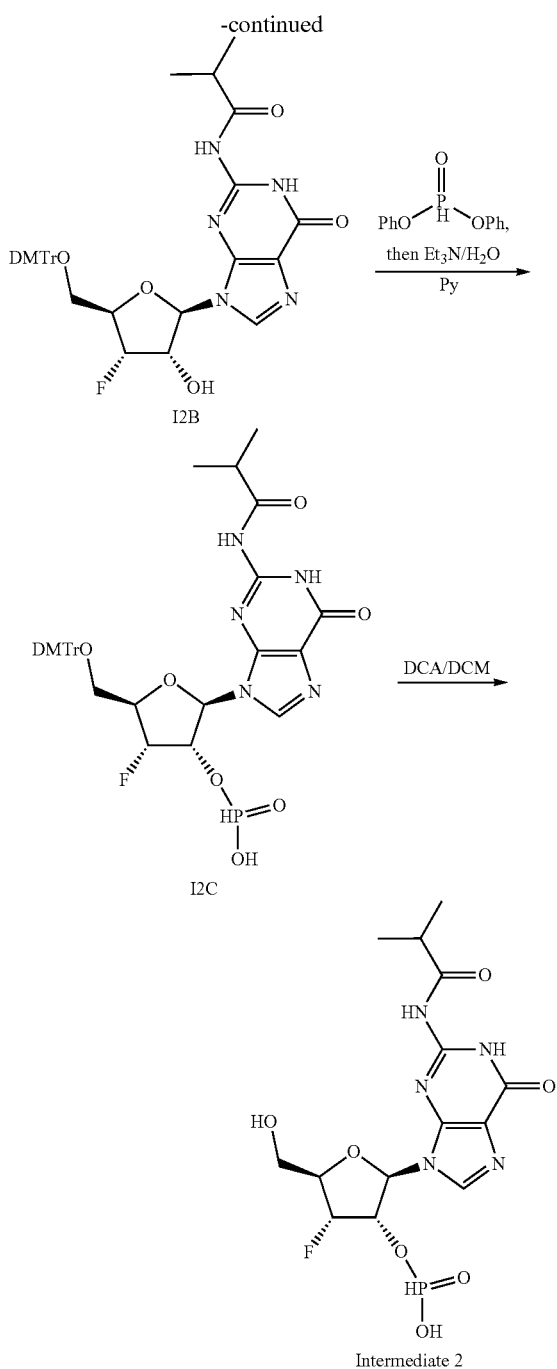

N-(9-((2R,3S,4S,5R)-4-Fluoro-3-hydroxy-5-(hydroxymethyl)tetrahydrofuran-2-yl)-6-oxo-6,9-dihydro-1H-purin-2-yl)isobutyramide (I2A)

To a rapidly stirred suspension of 2-amino-9-((2R,3S,4S,5R)-4-fluoro-3-hydroxy-5-(hydroxymethyl)tetrahydrofuran-2-yl)-1H-purin-6(9H)-one (974 mg, 3.41 mmol) in pyridine (20 mL) at −5° C. was added TMSCl (2.17 mL, 17.1 mmol) in a dropwise fashion. The bath was removed and the reaction mixture was allowed to stir at RT for 40 min, whereupon isobutyric anhydride (1.70 mL, 10.2 mmol) was added in a dropwise fashion. The reaction was stirred at RT for 2 hrs, and then quenched by the addition of MeOH (3.4 mL). After stirring at RT for 5 minutes, conc. NH$_4$OH (6.8 mL) was added in a dropwise fashion with intermittent cooling using a RT water bath. After stirring at RT for 1 hr the reaction mixture was concentrated to dryness under reduced pressure. To the residue was added DCM (12 mL) and MeOH (1.3 mL) and the resulting mixture was sonicated briefly, and then filtered. To the filtrate was added silica gel (8 g), and the mixture was concentrated under reduced pressure. The residue was purified by silica gel chromatography (0-10% MeOH/DCM) to give I2A (780 mg, 64%) as a white solid. LCMS m/z 356.2 (M+H)$^+$. $^1$H NMR (DMSO-d$_6$) δ 12.09 (br s, 1H), 11.68 (br s, 1H), 8.27 (s, 1H), 5.97 (d, J=6.3 Hz, 1H), 5.83 (d, J=8.3 Hz, 1H), 5.23 (t, J=5.4 Hz, 1H), 5.06 (dd, J=54.5, 4.1 Hz, 1H), 4.81-4.70 (m, 1H), 4.21 (dt, J=27.6, 4.5 Hz, 1H), 3.59 (t, J=4.9 Hz, 2H), 2.75 (hept, J=6.9 Hz, 1H), 1.11 (d, J=6.8 Hz, 6H). $^{19}$F NMR (DMSO-d$_6$) δ −197.48.

N-(9-((2R,3S,4S,5R)-5-((Bis(4-Methoxyphenyl)(phenyl)methoxy)methyl)-4-fluoro-3-hydroxytetrahydrofuran-2-yl)-6-oxo-6,9-dihydro-1H-purin-2-yl)isobutyramide (I2B)

To a solution of I2A (780 mg, 2.20 mmol) in pyridine (20 mL) at −5° C. was added DMTrCl (818 mg, 2.41 mmol) in one portion. The resulting mixture was stirred at RT for 3 hrs, and then concentrated under reduced pressure. The residue was redissolved in MeOH (24 mL) containing 1% Et$_3$N, and then silica gel (8 g) was added. The mixture was concentrated to dryness under reduced pressure. The residue was purified by silica gel chromatography (0-10% MeOH/DCM containing 1% Et$_3$N) to give I2B (1.20 g, 83%) as a white solid. LCMS m/z 658.4 (M+H)$^+$. $^1$H NMR (DMSO-d$_6$) δ 12.06 (br s, 1H), 11.59 (br s, 1H), 8.12 (s, 1H), 7.32 (d, J=7.0 Hz, 1H), 7.26-7.19 (comp, 7H), 6.82 (d, J=8.3 Hz, 2H), 6.80 (d, J=8.5 Hz, 2H), 6.06 (d, J=6.0 Hz, 1H), 5.85 (d, J=7.3 Hz, 1H), 5.13 (dd, J=54.0, 3.0 Hz, 1H), 4.94 (dq, J=22.6, 6.5 Hz, 1H), 4.27 (br dt, J=26.4, 3.6 Hz, 1H), 3.71 (s, 6H), 3.39 (dd, J=10.6, 5.7 Hz, 1H), 3.19 (dd, J=10.8, 3.8 Hz, 1H), 2.73 (hept, J=6.8 Hz, 1H), 1.12 (d, J=6.8 Hz, 6H). $^{19}$F NMR (DMSO-d$_6$) δ −198.0.

(2R,3S,4R,5R)-5-((Bis(4-methoxyphenyl)(phenyl)methoxy)methyl)-4-fluoro-2-(2-isobutyramido-6-oxo-1H-purin-9(6H)-yl)tetrahydrofuran-3-yl hydrogen phosphonate (I2C)

To a solution of I2B (1.20 g, 1.82 mmol) in pyridine (10 mL) was added diphenyl phosphite (1.05 mL, 5.48 mmol). The reaction mixture was stirred at RT for 20 min, and then cooled in an ice/acetone bath, whereupon Et$_3$N (1.8 mL) and H$_2$O (1.8 mL) were added. The bath was removed and the reaction mixture was stirred at RT for 40 min, and concentrated under reduced pressure. The residue was redissolved in MeOH (15 mL) containing 1% Et$_3$N, and then silica gel (5 g) was added. The mixture was concentrated under reduced pressure, and then the residue was purified by silica gel chromatography (0-7% MeOH/DCM containing 1% Et$_3$N). Concentration of appropriate fractions gave a product that contained inorganic phosphate and Et$_3$N salts. This was partitioned between DCM (70 mL) and 5% aq. NaHCO$_3$ (20 mL). The organic layer was removed, dried (Na$_2$SO$_4$), and then concentrated to give I2C (1.50 g, >quant) that was slightly contaminated with Et$_3$N salts. This material was used "as is" in subsequent transformations. LCMS m/z 722.3 (M+H)+. $^1$H NMR (CD$_3$OD) δ 8.13 (s, 1H), 7.44-7.42 (m, 2H), 7.33-7.17 (comp, 7H), 6.86-6.79 (comp, 4H), 6.79

(dd, J=632.0 Hz, 1.3 Hz, 1H), 6.19 (d, J=6.8 Hz, 1H), 5.84-5.74 (m, 1H), 5.41 (ddd, J=77.6, 4.5, 2.3 Hz, 1H), 4.49 (app dt, J=24.9, 2.3 Hz, 1H), 3.80 (s, 3H), 3.79 (s, 3H), 3.56-3.51 (m, 1H), 3.38-3.34 (m, 1H), 2.63 (hept, J=6.8 Hz, 1H), 1.23 (d, J=7.0 Hz, 3H), 1.20 (d, J=7.0 Hz, 3H). $^{19}$F NMR (CD$_3$OD) δ −200.22. $^{31}$P NMR (CD$_3$OD) δ 2.81.

(2R,3S,4R,5R)-4-Fluoro-5-(hydroxymethyl)-2-(2-isobutyramido-6-oxo-1H-purin-9(6H)-yl)tetrahydro-furan-3-yl hydrogen phosphonate (Intermediate 2)

To a suspension of I2C (1.32 g, 1.83 mmol) in DCM (10 mL) was added H$_2$O (329 mg, 18.3 mmol) followed by a solution of DCA (1.36 mL, 16.5 mmol) in DCM (15 mL). The reaction mixture was stirred and sonicated occasionally for 20 min at RT, and then TES (15 mL) was added. After stirring and sonicating for an additional 1.5 hrs, pyridine (3 mL) was added. The mixture was concentrated under reduced pressure, and the residue was purified by RP-MPLC (C18 column, 0-30% ACN/H$_2$O containing 0.04% NH$_4$HCO$_3$) to give Intermediate 2 (410 mg, 53%) as a white solid. LCMS (Method C, T$_R$=0.93 min) m/z 418.2 (M−H)$^−$. $^1$H NMR (CD$_3$OD) δ 8.35 (s, 1H), 6.74 (dd, J=631.7, 1.3 Hz, 1H), 6.20 (d, J=6.8 Hz, 1H), 5.43-5.25 (comp, 2H), 4.46-4.40 (m, 1H), 3.85 (d, J=3.5 Hz, 2H), 2.77 (hept, J=6.8 Hz, 1H), 1.27 (d, J=7.0 Hz, 6H). $^{19}$F NMR (CD$_3$OD) δ −200.82. $^{31}$P NMR (CD$_3$OD) δ 2.42.

Example 1

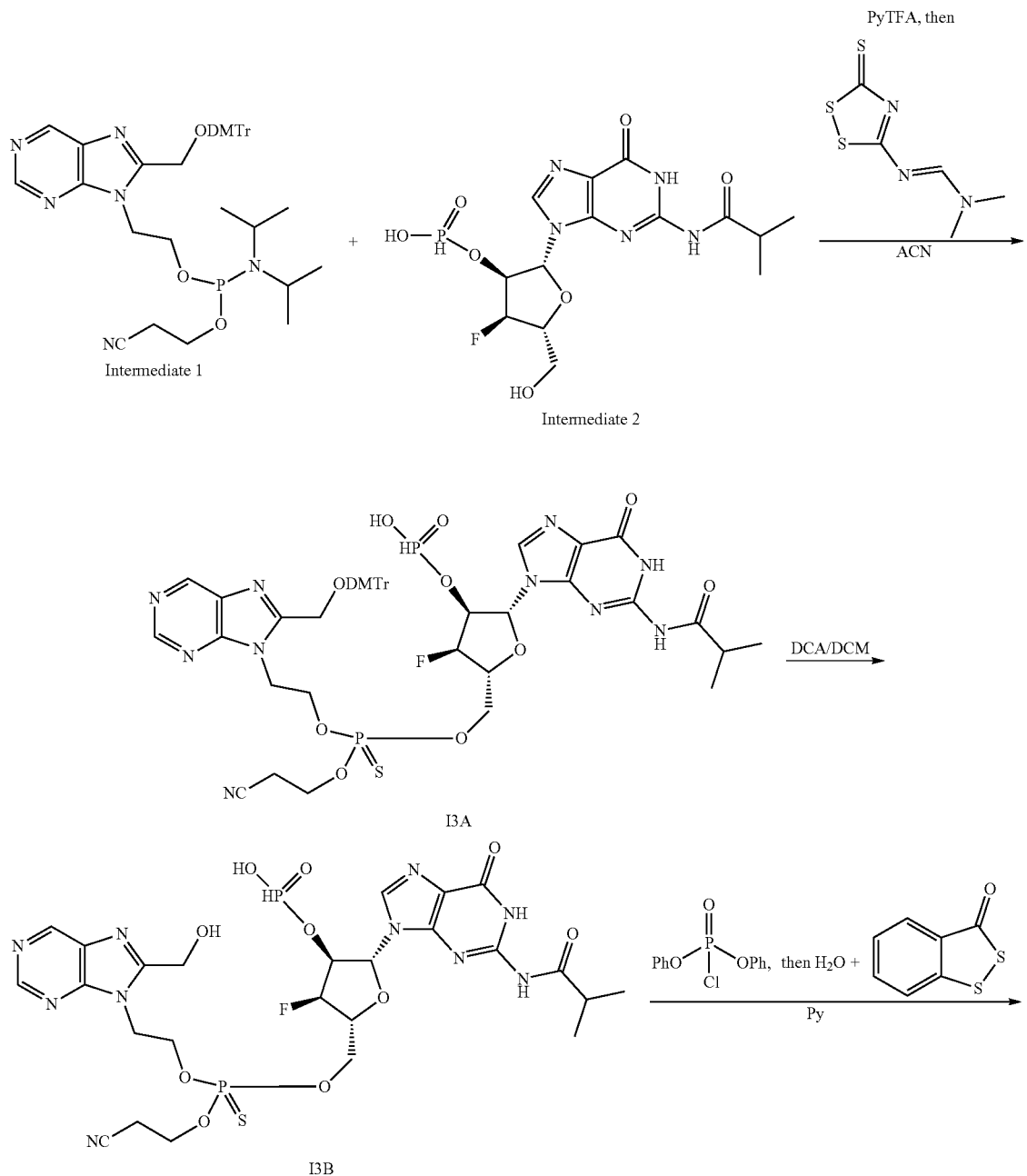

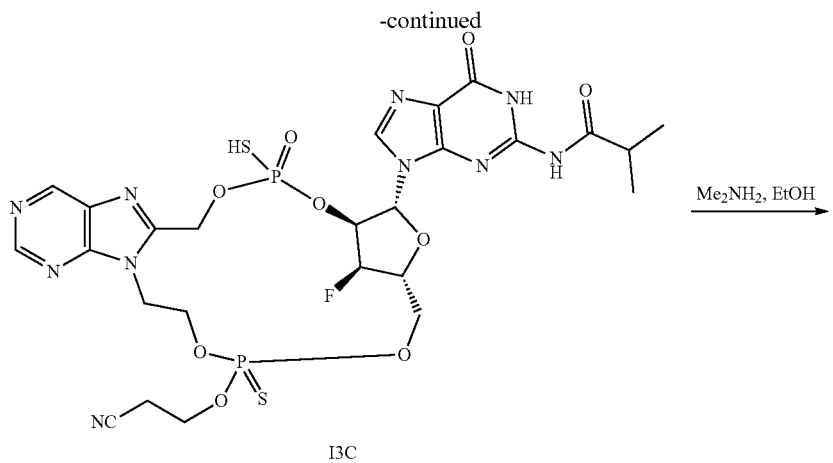

I3C

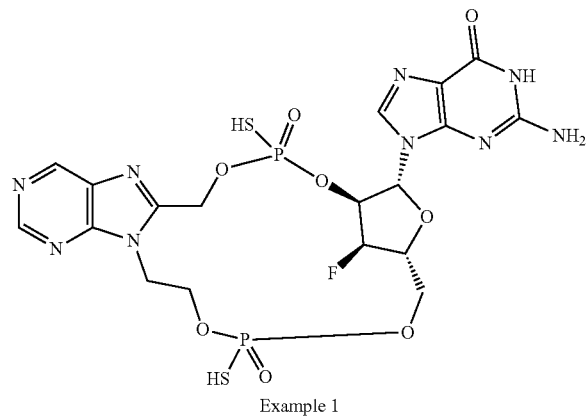

Example 1

(2R,3S,4R,5R)-5-(0(2-(84(Bis(4-methoxyphenyl)(phenyl)methoxy)methyl)-9H-purin-9-yl)ethoxy)(2-cyanoethoxy)phosphorothioyl)oxy)methyl)-4-fluoro-2-(2-isobutyramido-6-oxo-1H-purin-9(6H)-yl)tetrahydrofuran-3-yl hydrogen phosphonate (I3A)

Coupling-Oxidative Sulfurization (Coupling Method A)

A suspension of Intermediate 1 (810 mg, 1.16 mmol) and crushed, freshly activated 3 Å MS (200 mg) in ACN (6 mL) was stirred with occasional sonication for 45 minutes under $N_2$. In the meantime, a suspension of Intermediate 2 (406 mg, 0.970 mmol), Py·TFA (374 mg, 1.94 mmol), and crushed, freshly activated 3 Å MS (200 mg) in ACN (4 mL) was stirred with occasional sonication for 45 min under $N_2$. The supernatant containing Intermediate 1 was added to the suspension of Intermediate 2 in a dropwise fashion, via syringe. The flask and residual MS that contained Intermediate 1 was washed with ACN (2 mL) and the supernatant was again added to the mixture containing Intermediate 2. The resulting mixture was stirred at RT for 45 min, whereupon DDTT (219 mg, 1.07 mmol) was added in one portion. The reaction mixture was stirred at RT for 1 hr, and then filtered to remove the sieves. The filtrate was concentrated under reduced pressure, and the residue was purified by RP-MPLC (C18, 10-100% ACN/$H_2O$ containing 0.04% $NH_4HCO_3$) to give I3A (462 mg, 46% of a 1.0:1.2 mixture of diastereomers by $^{31}P$ NMR) as a pale yellow solid. LCMS m/z 1045.1 (M–H)$^-$. $^{19}F$ NMR (CD$_3$OD) δ –202.16, –202.45. $^{31}P$ NMR (CD$_3$OD) δ P=S$_{major}$ 68.05, P=S$_{minor}$ 67.69, P=O$_{major/minor}$ 2.55.

(2R,3S,4R,5R)-5-((((2-Cyanoethoxy)(2-(8-(hydroxymethyl)-9H-purin-9-yl)ethoxy)phosphorothioyl)oxy)methyl)-4-fluoro-2-(2-isobutyramido-6-oxo-1H-purin-9(6H)-yl)tetrahydrofuran-3-yl hydrogen phosphonate (I3B)

To a rapidly stirred mixture of I3A (462 mg, 0.440 mmol, 1.0:1.2 mixture of diastereomers) and $H_2O$ (80.0 mg, 4.44 mmol) in DCM (7 mL) was added DCA (512 mg, 3.97 mmol) in DCM (7 mL). After 15 min at RT, Et$_3$SiH (12.3 mL) was introduced and the reaction mixture was stirred for 1 hr. Pyridine (1.4 mL) and MeOH (1.4 mL) were added, and then the reaction mixture was concentrated under reduced pressure. The residue was dissolved in MeOH (7 mL), and silica gel (4 g) was added. The mixture was concentrated to dryness, and purified by silica gel chromatography (0-100% MeOH/DCM) to give I3B (288 mg, 88% of a 1.0:1.1 mixture of diastereomers by $^{31}P$ NMR) as a white solid. LCMS m/z 743.1 (M–H)$^-$. $^{19}F$ NMR (CD$_3$OD) δ –201.64, –201.75. $^{31}P$ NMR (CD$_3$OD) δ P=S$_{major}$ 68.18, P=S$_{minor}$ 67.89, P=O$_{major/minor}$ 2.55.

N-{9-[(1S,21R,23R,24R)-18-(2-Cyanoethoxy)-24-fluoro-3-oxo-3-sulfanyl-18-sulfanylidene-2,4,17,19,22-pentaoxa-7,10,12,14-tetraaza-3lambda5,18lambda5-diphosphatetracyclo[19.2.1.06,14.08,13]tetracosa-6,8,10,12-tetraen-23-yl]-6-oxo-6,9-dihydro-1H-purin-2-yl}-2-methylpropanamide (I3C)

Cyclization-Oxidative Sulfurization (Cyclization Method A)

To dry pyridine (25 mL) cooled to –30° C. was added diphenyl phosphoryl chloride (746 µL, 3.60 mmol). After 5 min, a solution of I3B (134 mg, 0.180 mmol) in pyridine (7 mL) was added in a dropwise fashion over 20 min while maintaining the bath temperature between −35 and −30° C. After stirring at −30° C. for 40 min, H₂O (162 mg, 9.00 mmol) and 3H-benzo[c][1,2]dithiol-3-one (45 mg, 0.27 mmol) were added in rapid succession. The −30° C. bath was replaced with a RT bath and the reaction mixture was stirred at this temperature for 1 hr. The reaction mixture was cooled to 0° C., then quenched by adding a solution of sodium thiosulfate (112 mg) in H₂O (30 mL) in a dropwise fashion. The bath was removed and the mixture was stirred at RT for 5 min, partially concentrated (to ca. 5 mL) under reduced pressure, then purified using RP-MPLC (C18, 0-50% ACN/H₂O containing 0.04% NH₄HCO₃) to give I3C (112 mg, 82% of a 1.0:1.4:2.3:3.0 mixture of diastereomers by $^{31}$P NMR) as a white solid. LCMS (Method C) m/z 757.1 (M−H)⁻. $^{19}$F NMR (CD₃OD) δ −196.82 (minor), −197.44 (minor), −198.73 (major), −199.48 (major). $^{31}$P NMR (CD₃OD) δ 69.01 (minor), 67.89 (major), 65.51 (minor), 65.27 (major), 60.69 (minor), 60.14 (minor), 57.54 (major), 56.54 (major).

(1S,21R,23R,24R)-23-(2-Amino-6-oxo-6,9-dihydro-1H-purin-9-yl)-24-fluoro-3,18-disulfanyl-2,4,17,19,22-pentaoxa-7,10,12,14-tetraaza-3lambda5,18lambda5-diphosphatetracyclo[19.2.1.0⁶,¹⁴.0⁸,¹³]tetracosa-6,8(13),9,11-tetraene-3,18-dione (Example 1)

A solution of I3C (112 mg, 0.150 mmol, 1.0:1.4:2.3:3.0 mixture of diastereomers) in MeNH₂/EtOH (33%, 10 mL) was stirred at RT for 5 hrs, and then concentrated under reduced pressure. The residue was purified by RP-HPLC (Sunfire Prep C18, 5 μm, 19×100 mm column eluting with 0-30% ACN/H₂O containing 0.04% NH₄HCO₃, Flow rate=7 mL/min) to give 4 pure diastereomers (Diastereomer A: T$_R$=8.1 min, 11.9 mg; Diastereomer B: T$_R$=9.7 min, 6.4 mg; Diastereomer C: T$_R$=11.2 min, 22.0 mg; Diastereomer D: T$_R$=11.8 min, 7.4 mg; Total: 47.7 mg, 51%) of Example 1. Example 1A (Diastereomer A): LCMS (Method D, T$_R$=1.17 min) m/z 634.0 (M−H)⁻. $^1$H NMR (CD₃OD) δ 9.06 (s, 1H), 8.97 (s, 1H), 8.15 (s, 1H), 6.12 (d, J=8.3 Hz, 1H), 5.65 (dd, J=53.2, 3.5 Hz, 1H), 5.50 (dd, J=12.8, 7.3 Hz, 1H), 5.41-5.28 (m, 1H), 5.07-4.54 (comp, 5H), 4.42-4.35 (m, 2H), 4.08 (app dt, J=11.3, 2.5 Hz, 1H). $^{19}$F NMR (CD₃OD) δ −199.75. $^{31}$P NMR (CD₃OD) δ 57.20, 57.05. Example 1B (Diastereomer B): LCMS (Method D, T$_R$=1.12 min) m/z 634.0 (M−H)⁻. $^1$H NMR (CD₃OD) δ 9.06 (s, 1H), 8.97 (s, 1H), 8.33 (s, 1H), 6.10 (d, J=8.3 Hz, 1H), 5.80-5.68 (m, 1H), 5.50 (dd, J=12.8, 7.3 Hz, 1H), 5.23-4.41 (comp, 8H), 4.01-3.97 (m, 1H) $^{19}$F NMR (CD₃OD) δ −198.64. $^{31}$P NMR (CD₃OD) δ 60.53, 57.40. Example 1C (Diastereomer C): LCMS (Method D, T$_R$=1.20 min) m/z 634.0 (M−H)⁻. $^1$H NMR (CD₃OD) δ 9.10 (s, 1H), 8.98 (s, 1H), 7.90 (s, 1H), 6.09 (d, J=8.5 Hz, 1H), 5.60 (dd, J=53.2, 3.8 Hz, 1H), 5.53 (dd, J=12.8, 7.8 Hz, 1H), 5.40-5.28 (comp, 6H), 4.34-4.30 (m, 1H), 4.40-4.01 (m, 1H). $^{19}$F NMR (CD₃OD) δ −199.24. $^{31}$P NMR (CD₃OD) δ 57.05, 56.14. Example 1D (Diastereomer D): LCMS (Method D, T$_R$=1.24 min) m/z 634.0 (M−H)⁻. $^1$H NMR (CD₃OD) δ 9.06 (s, 1H), 8.97 (s, 1H), 8.17 (s, 1H), 6.12 (d, J=8.3 Hz, 1H), 5.72-5.59 (m, 1H), 5.48 (dd, J=13.1, 7.8 Hz, 1H), 5.32-4.44 (comp, 7H), 4.36 (ddd, J=11.3, 8.3, 2.3 Hz, 1H), 4.12-4.10 (m, 1H). $^{19}$F NMR (CD₃OD) δ −197.59. $^{31}$P NMR (CD₃OD) δ 60.29, 58.08.

The invention claimed is:

1. A method for treating solid tumors comprising administering to a patient in need of treatment for a solid tumor a therapeutically effective amount of a compound of formula 1

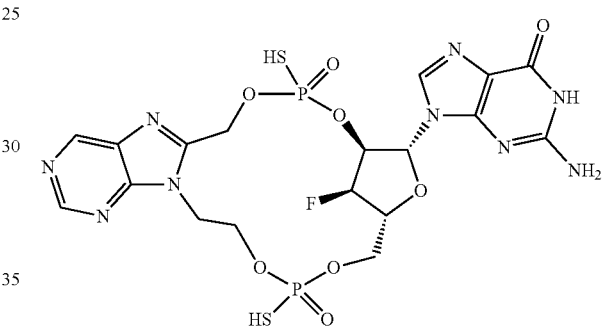

or pharmaceutically acceptable salt thereof.

2. The method of claim 1 wherein said compound of formula 1 is administered as an aqueous solution.

3. The method of claim 1 wherein the compound is administered intravenously.

4. The method of claim 1 wherein said solid tumor is a colon carcinoma.

* * * * *